(12) United States Patent
Bhargava et al.

(10) Patent No.: US 12,346,410 B2
(45) Date of Patent: Jul. 1, 2025

(54) TISSUE MICROENVIRONMENT ANALYSIS BASED ON TIERED CLASSIFICATION AND CLUSTERING ANALYSIS OF DIGITAL PATHOLOGY IMAGES

(71) Applicant: The Board of Trustees of the University of Illinois, Urbana, IL (US)

(72) Inventors: Rohit Bhargava, Urbana, IL (US); Shachi Mittal, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 809 days.

(21) Appl. No.: 17/449,774

(22) Filed: Oct. 1, 2021

(65) Prior Publication Data

US 2022/0108123 A1     Apr. 7, 2022

Related U.S. Application Data

(60) Provisional application No. 63/086,473, filed on Oct. 1, 2020.

(51) Int. Cl.
*G06F 18/2431* (2023.01)
*G06F 18/23213* (2023.01)
(Continued)

(52) U.S. Cl.
CPC .... *G06F 18/2431* (2023.01); *G06F 18/23213* (2023.01); *G06N 3/08* (2013.01);
(Continued)

(58) Field of Classification Search
CPC ............ G06T 7/0012; G06T 7/11; G06T 2207/20084; G06T 2207/30068; G06T 2207/30096; G06V 10/40; G06V 10/95; G06V 2201/03; G16H 10/40; G16H 15/00; G16H 30/40; G06F 18/23213; G06N 3/08

See application file for complete search history.

(56) References Cited

U.S. PATENT DOCUMENTS

| 12,085,568 B2 * | 9/2024 | Agus ................ G06F 18/211 |
| 2017/0091937 A1 * | 3/2017 | Barnes .............. G06V 10/806 |

OTHER PUBLICATIONS

Digital Assessment of Breast Tissue Images for Comprehensive Tumor and Microenvironment Analysis. (Year: 2019).*

(Continued)

*Primary Examiner* — Daniel G Mariam
(74) *Attorney, Agent, or Firm* — Quarles & Brady LLP

(57) ABSTRACT

Segmentation or other classification of digital pathology images with a deep learning model allows for sophisticated spatial features for cancer diagnosis to be extracted in an automated, fast, and accurate manner. A tiered analysis of tissue structure based in part on deep learning methods is provided. First, tissues depicted in a digital pathology image are segmented into cellular compartments (e.g., epithelial and stromal compartments). Second, the heterogeneity in the different cellular compartments are examined based on a clustering algorithm. Tissue can then be characterized in terms of inertia (or other spatial measures or features), which can be used to recognize disease. In some instances, multi-dimensional inertia (i.e., inertia computed in different cellular compartments or clustered components) can be used as an indicator of disease and its outcome.

17 Claims, 17 Drawing Sheets
(14 of 17 Drawing Sheet(s) Filed in Color)

(51) Int. Cl.
  G06N 3/08    (2023.01)
  G06T 7/00    (2017.01)
  G06T 7/11    (2017.01)
  G06V 10/40   (2022.01)
  G06V 10/94   (2022.01)
  G16H 10/40   (2018.01)
  G16H 15/00   (2018.01)
  G16H 30/40   (2018.01)

(52) U.S. Cl.
  CPC .............. *G06T 7/0012* (2013.01); *G06T 7/11* (2017.01); *G06V 10/40* (2022.01); *G06V 10/95* (2022.01); *G16H 10/40* (2018.01); *G16H 15/00* (2018.01); *G16H 30/40* (2018.01); *G06T 2207/20084* (2013.01); *G06T 2207/30068* (2013.01); *G06T 2207/30096* (2013.01); *G06V 2201/03* (2022.01)

(56) References Cited

OTHER PUBLICATIONS

Abdel-Zaher, Ahmed M., et al. "Breast cancer classification using deep belief networks." Expert Systems with Applications 46 (2016): 139-144.
Araujo, Teresa et al.. "Classification of breast cancer histology images using convolutional neural networks." PloS one 12, No. 6 (2017): e0177544.
Bahreini, Fatemeh et al.. "A meta-analysis on concordance between immunohistochemistry (IHC) and fluorescence in situ hybridization (FISH) to detect HER2 gene overexpression in breast cancer." Breast cancer 22, No. 6 (2015): 615-625.
Beck, Andrew H. et al. "Systematic analysis of breast cancer morphology uncovers stromal features associated with survival." Science translational medicine 3, No. 108 (2011): 108ra113-108ra113.
Bychkov, Dmitrii et al. "Deep learning based tissue analysis predicts outcome in colorectal cancer." Scientific reports 8, No. 1 (2018): 1-11.
Chollet, Francois. "Xception: Deep learning with depthwise separable convolutions." In Proceedings of the IEEE conference on computer vision and pattern recognition, pp. 1251-1258. 2017.
Conklin, Matthew W. et al. "Why the stroma matters in breast cancer: insights into breast cancer patient outcomes through the examination of stromal biomarkers." Cell adhesion & migration 6, No. 3 (2012): 249-260.
Costarelli, Leopoldo et al. "Intraductal proliferative lesions of the breast—terminology and biology matter: premalignant lesions or preinvasive cancer?." International Journal of Surgical Oncology 2012 (2012).
Coudray, Nicolas, et al. "Classification and mutation prediction from non-small cell lung cancer histopathology images using deep learning." Nature medicine 24.10 (2018): 1559-1567.
Dong, Fei, et al. "Computational pathology to discriminate benign from malignant intraductal proliferations of the breast." PloS one 9.12 (2014): e114885.
Doyle, Scott, et al. "Automated grading of breast cancer histopathology using spectral clustering with textural and architectural image features." 2008 5th IEEE International Symposium on Biomedical Imaging: From Nano to Macro. IEEE, 2008.
Ehteshami Bejnordi, Babak, et al. "Diagnostic assessment of deep learning algorithms for detection of lymph node metastases in women with breast cancer." Jama 318.22 (2017): 2199-2210.
Ehteshami Bejnordi, Babak, et al. "Using deep convolutional neural networks to identify and classify tumor-associated stroma in diagnostic breast biopsies." Modern Pathology 31.10 (2018): 1502-1512.
Ellis, Ian O. "Intraductal proliferative lesions of the breast: morphology, associated risk and molecular biology." Modern pathology 23.2 (2010): S1-S7.
Elmore, Joann G., et al. "Diagnostic concordance among pathologists interpreting breast biopsy specimens." Jama 313.11 (2015): 1122-1132.
Ertosun, Mehmet Gunhan, et al. "Automated grading of gliomas using deep learning in digital pathology images: a modular approach with ensemble of convolutional neural networks." AMIA annual symposium proceedings. vol. 2015. American Medical Informatics Association, 2015.
Finak, Greg, et al. "Stromal gene expression predicts clinical outcome in breast cancer." Nature medicine 14.5 (2008): 518-527.
Gecer, Baris, et al. "Detection and classification of cancer in whole slide breast histopathology images using deep convolutional networks." Pattern recognition 84 (2018): 345-356.
Ghaznavi, Farzad, et al. "Digital imaging in pathology: whole-slide imaging and beyond." Annu Rev Pathol 8.1 (2013): 331-359.
Giussani, Marta, et al. "Extracellular matrix proteins as diagnostic markers of breast carcinoma." Journal of cellular physiology 233.8 (2018): 6280-6290.
Guo, Yang, et al. "Identification of cancer subtypes by integrating multiple types of transcriptomics data with deep learning in breast cancer." Neurocomputing 324 (2019): 20-30.
Gurcan, Metin N., et al. "Histopathological image analysis: A review." IEEE reviews in biomedical engineering 2 (2009): 147-171.
Hanahan, Douglas, et al. "Accessories to the crime: functions of cells recruited to the tumor microenvironment." Cancer cell 21.3 (2012): 309-322.
Harvey, Hugh, et al. "Deep learning in breast cancer screening." Artificial Intelligence in Medical Imaging. Springer, Cham, 2019. 187-215.
He, Kaiming, et al. "Deep residual learning for image recognition." Proceedings of the IEEE conference on computer vision and pattern recognition. 2016.
Hu, Min, et al. "Distinct epigenetic changes in the stromal cells of breast cancers." Nature genetics 37.8 (2005): 899-905.
Huang, Yongxiang, et al. "Improving high resolution histology image classification with deep spatial fusion network." Computational Pathology and Ophthalmic Medical Image Analysis. Springer, Cham, 2018. 19-26.
Jain, Rohit K., et al. "Atypical ductal hyperplasia: interobserver and intraobserver variability." Modern Pathology 24.7 (2011): 917-923.
Jia, Zhenyu, et al. "Tumor microenvironment: prospects for diagnosis and prognosis of prostate cancer based on changes in tumor-adjacent stroma." Precision Molecular Pathology of Prostate Cancer. Springer, Cham, 2018. 259-275.
Komura, Daisuke, et al.. "Machine learning methods for histopathological image analysis." Computational and structural biotechnology journal 16 (2018): 34-42.
Kumar S., et al. "Change in the microenvironment of breast cancer studied by FTIR imaging." Analyst 138.14 (2013): 4058-4065.
Litjens, Geert, et al. "Deep learning as a tool for increased accuracy and efficiency of histopathological diagnosis." Scientific reports 6.1 (2016): 1-11.
Mao, Yan, et al. "Stromal cells in tumor microenvironment and breast cancer." Cancer and Metastasis Reviews 32.1 (2013): 303-315.
Mercan, Ezgi, et al. "Assessment of machine learning of breast pathology structures for automated differentiation of breast cancer and high-risk proliferative lesions." JAMA network open 2.8 (2019): e198777-e198777.
Mishra, Rashika, et al. "Convolutional neural network for histopathological analysis of osteosarcoma." Journal of Computational Biology 25.3 (2018): 313-325.
Mittal, Shachi, et al. "Digital assessment of stained breast tissue images for comprehensive tumor and microenvironment analysis." Frontiers in bioengineering and biotechnology (2019): 246.
Pantanowitz, Liron, et al. "Review of the current state of whole slide imaging in pathology." Journal of pathology informatics 2.1 (2011): 36.
Postavaru, Stefan, et al. "Adaptation of deep convolutional neural networks for cancer grading from histopathological images." International Work-Conference on Artificial Neural Networks. Springer, Cham, 2017.

(56) References Cited

OTHER PUBLICATIONS

Simonyan, Karen, et al. "Very deep convolutional networks for large-scale image recognition." arXiv preprint arXiv:1409.1556 (2014).
Stalhammar, Gustav, et al. "Digital image analysis outperforms manual biomarker assessment in breast cancer." Modern Pathology 29.4 (2016): 318-329.
Veta, Mitko, et al. "Breast cancer histopathology image analysis: A review." IEEE transactions on biomedical engineering 61.5 (2014): 1400-1411.
Williams, Bethany Jill, et al. "Future-proofing pathology: the case for clinical adoption of digital pathology." Journal of clinical pathology 70.12 (2017): 1010-1018.

* cited by examiner

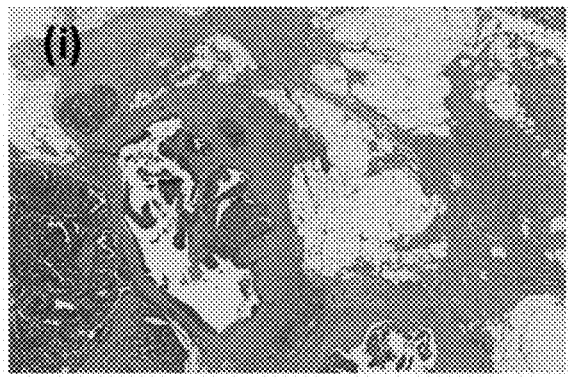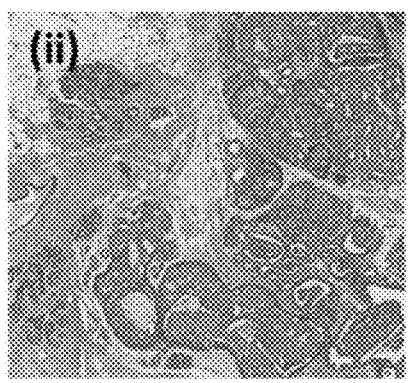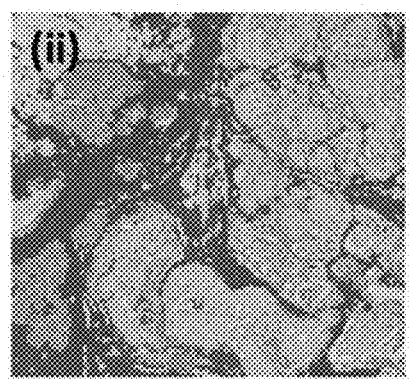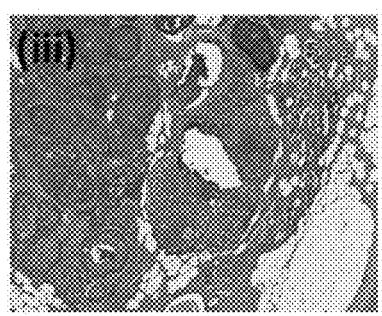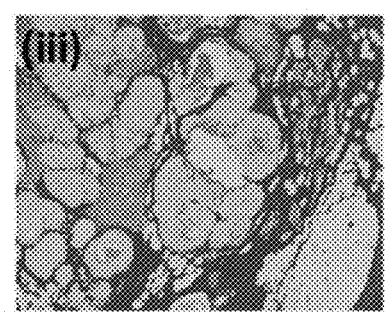
FIG. 4A  FIG. 4B

TISSUE MICROENVIRONMENT ANALYSIS BASED ON TIERED CLASSIFICATION AND CLUSTERING ANALYSIS OF DIGITAL PATHOLOGY IMAGES

CROSS-REFERENCE TO RELATED APPLICATIONS

This application claims the benefit of U.S. Provisional Patent Application Ser. No. 63/086,473, filed on Oct. 1, 2020, and entitled "DIGITAL METHODS AND SYSTEMS FOR BREAST CANCER DETECTION AND DISTINGUISHING BETWEEN THE DIFFERENT NON-CANCEROUS BUT RISKY LESIONS."

STATEMENT REGARDING FEDERALLY SPONSORED RESEARCH

This invention was made with government support under EB009745 awarded by the National Institutes of Health. The government has certain rights in the invention.

BACKGROUND

Annually, about a million breast biopsies are performed in the United States, out of which typically a quarter receive a cancer diagnosis. The remaining benign or in-situ patient cases, that are combined into the category of intraductal lesions of the breast, are susceptible to over or under diagnosis. Current standards for separating benign intraductal lesions from ductal carcinoma in-situ ("DCIS") rely on visual inspection of morphometric features. This involves manual interpretation of architectural and cytological patterns in the epithelial compartments of the tissue. This can often be time consuming and lead to discordant measurements. Intraductal proliferations are primarily composed of Usual Ductal Hyperplasia ("UDH"), Atypical Ductal Hyperplasia ("ADH") and DCIS.

The treatment profiles for all these three categories are different making it important to precisely identify these lesions. UDH lesion does not require any further management whereas in ADH, the area of interest in excised out and DCIS is treated by either an excision or complete mastectomy followed by radiation/neoadjuvant therapy.

It has been previously reported that a 48% concordance rate is achieved amongst pathologists to separate atypical hyperplasia from in-situ carcinoma. Deep learning models can enable the identification of global and local textural patterns that are indicative of an altered epithelial profile. This enables the mapping of different architectural patterns of epithelium into precise risk and disease categories.

Recently, there have been some advances in digital approaches for breast cancer analysis. However, there are only a few studies that investigated pre-invasive lesions and early stage tumor. The most recent study reports a 70% accuracy to distinguish benign samples from atypia and DCIS. Also, one of the limitations of this study is that the proposed model works only on selected regions of interest making it difficult to fully extend to large slide sections.

Currently, the standard of care technology to identify the above-mentioned benign proliferations and DCIS is microscopic evaluation of stained slides by a trained human (e.g., a pathologist). This assessment is subjective, prone to measurement error and is time consuming. This can also often lead to the problem of over diagnoses. The proposed methodology will assist pathologist towards precise diagnostics in an objective and rapid manner.

Recently, there have been some advances in digital approaches for breast cancer analysis. However, there are only a few studies that investigated pre-invasive lesions and early stage tumor. One such study reported a 70% accuracy to distinguish benign samples from atypia and DCIS, and used a model that works only on selected regions of interest, thereby making it difficult to fully extend to large slide sections.

The current clinical pipeline for cancer diagnosis involves human expert evaluation of large sections of tissue stained with dyes or a variety of specialized molecular markers. Increasing cancer incidence rates put an increased burden on pathologists worldwide, as limited resources and limited growth of trained medical personnel are subjected to greater strains. In addition to the emerging needs for better diagnoses, challenges lie in accurate diagnoses using current methods as well.

Morphometric features form the bases of decisions today; however, difficulty in recognition of subtle morphologic changes and the process of assigning a discrete grade to a continuum of disease often makes the diagnosis prone to under or overdiagnosis. With the advent of whole slide imaging, digitized versions of stained slides are available and advanced computational analysis can be readily applied. Digital screening of images, even for simple classifications like "cancer" versus "no cancer," can help reduce the pathologist's workload by triaging and focusing on specific areas as well as alerting them to borderline cases.

Deep convolutional neural networks ("CNNs") are rising in popularity as a method for image processing in medicine, due to their inherent ability to automatically extract features, ranging from those very general to those very specific to the problem under consideration. Histopathology is an area where the CNN architectures can play an important role due to the intricacy of the decisions and the abundance of data resulting from routine patient screening, digital archiving of data, and advances in imaging. Depending on the quality of the histopathological images, a CNN architecture offers great flexibility and enables a variety of choices. For example, methods have been proposed to work directly with the available resolution if this is low, or on patches from high resolution images with the multiple decisions being further integrated by different techniques.

From hand-crafted architectures to pre-trained networks or residual models, CNNs have gained importance in the last few years in their use for tissue segmentation. One area of active application is in diagnosing and understanding breast cancer. While progress has been made in mimicking traditional processes involving epithelial transformations, a still unmet avenue to improved diagnoses is the use of the tumor microenvironment, both from conventional microenvironment measures and in using emerging imaging techniques.

SUMMARY OF THE DISCLOSURE

The present disclosure addresses the aforementioned drawbacks by providing A method for characterizing a tissue based on analysis of digital pathology images of the tissue. The method includes accessing segmented digital pathology image data with a computer system. The segmented digital pathology image data include digital pathology images of a tissue that have been segmented into two or more different cellular compartments of the tissue. The segmented digital pathology image data are applied to a clustering algorithm using the computer system, generating output as clustered feature data including clusters of the segmented digital pathology image data that indicate separated tissue microenvironment components of the tissue. Spatial feature parameter data, such as inertia, are computed for clusters in the clustered feature data using the computer system. A report is then generated with the computer system, where the report characterizes the tissue based on the spatial feature parameter data, wherein the report indicates a likelihood of disease in the tissue.

It is another aspect of the present disclosure to provide a method for analyzing digital pathology images of a tissue. The method includes accessing digital pathology image data with a computer system, where the digital pathology image data include digital pathology images of breast tissue. A convolutional neural network is accessed with the computer system, where the convolutional neural network has been trained on training data to separate different cellular components present in a digital pathology image. The digital pathology image data are applied to the convolutional neural network using the computer system, generating output as classified feature data identifying epithelial breast cells and stromal cells from their microenvironment. The microenvironment is analyzed to observe different constituent cells using the computer system to perform clustering of the classified feature data. Breast cancer is categorized by combined effects of stromal and epithelial inertia of the clustering of the classified feature data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A and 4B shows H&E images (FIG. 4A) and the corresponding classified images (FIG. 4B) in accordance with an embodiment of the present disclosure.

FIG. 10A shows H&E stained images from two different surgical samples and FIG. 10B shows the resulting classified images generated by applying those H&E images to the deep learning model. FIG. 10C shows H&E stained images from the tissue microarray for three different patients with distinct disease states, and FIG. 10D shows the resulting classified images generated by applying those H&E images to the deep learning model.

FIG. 12A shows a benign case with epithelial clustering (top), stromal clustering (middle), and H&E stained image (bottom). The inset (i) corresponds to zoomed in views from images in FIG. 12A. FIG. 12B shows a ductal carcinoma case with epithelial and stromal clustering along with the stained image, and where the inset (ii) corresponds to zoomed in views from images in FIG. 12B. FIG. 12C shows a lobular carcinoma case with clustering and ground truth comparison, and where the inset (iii) corresponds to zoomed regions from images in FIG. 12C.

FIG. 14A is a scatter plot separating patients from different disease states based on normalized inertia. FIG. 14B is a Receiver Operating Characteristic ("ROC") curve of using inertia as a cancer detection tool. The decision boundary shown in the figure is an illustration of one of the points on the ROC curve. All patients belonging to the fourth quadrant are labeled as normal.

DETAILED DESCRIPTION

Figure 1:
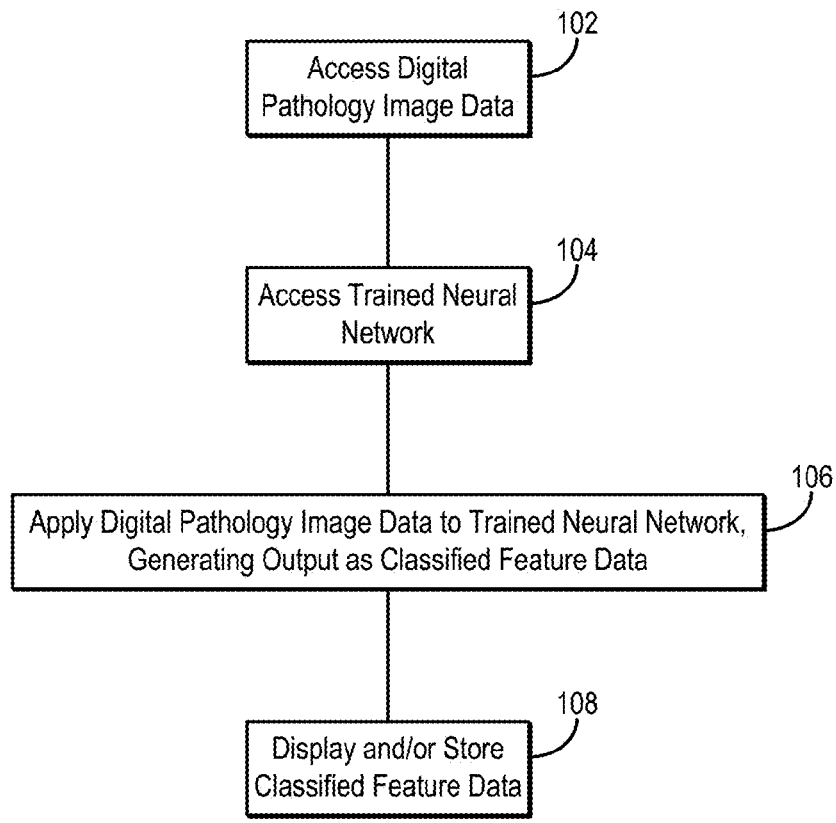
FIG. 1 is a flowchart setting forth the steps of an example method for generating classified feature data by applying digital pathology image data to a deep learning model, such as a neural network, where the classified feature data may indicate a classification or segmentation of the digital pathology image data.

Described here are systems and methods for processing digital pathology image data using a deep learning model in order to separate, segment, or otherwise classify different regions of digital pathology images. The digital pathology image data can include, for example, images (e.g., digital images) of stained slides of large surgical specimens.

The present disclosure provides a deep learning scheme for digital tissue segmentation using digital pathology images, which can further be used to extract sophisticated spatial features for cancer diagnosis in an automated, fast, and accurate manner. In some embodiments, the disclosed systems and methods implement a tiered analysis of tissue structure as deep learning methods were applied. First, tissues depicted in a digital pathology image are segmented into cellular compartments (e.g., epithelial and stromal compartments). Second, the heterogeneity in the different cellular compartments are examined based on a clustering algorithm. For example, applying a clustering algorithm to stromal compartments can result in separation of tissue microenvironment components like immune cells and cancer associated fibroblasts. A simple and interpretable characterization of the tissue in terms of inertia (or other spatial measures or features) can then be used to recognize disease. In some embodiments, multidimensional inertia (i.e., inertia computed in different cellular compartments or clustered components) can be used as an indicator of disease and its outcome, without needing additional resources or disruption to the current workflow.

The disclosed analytics tool can be integrated with whole slide scanners for interactive and real time sample analysis to aid human experts. Examples described in the present disclosure focus on simultaneously using the epithelial and stromal signatures to separate different diseased states. Additionally or alternatively, supervised classification schemes along with other tissue predictors can be implemented. More spatial features and detailed understanding of the tumor and the microenvironment can lead to increased insight into digital characterization of breast cancer (or other cancers) using conventionally stained images.

In some aspects, the disclosed systems and methods are capable of classifying digital pathology image data on the basis of a pathology class type, such as by separating benign breast tissue lesions (normal, usual hyperplasia, and atypical hyperplasia) from DCIS with high accuracy, (e.g., an accuracy of 90% or about 90%). Advantageously, the systems and methods described in the present disclosure are capable of achieving this high level of accuracy of classifying digital pathology image data on whole slide image sections, rather than just smaller regions-of-interest within an image. Because spatial patterns of an entire image are estimated, stromal alterations can be indirectly incorporated in the deep learning model making it more comprehensive for aiding in the diagnosis of disease and disease types (e.g., breast cancer types including DCIS). As a result, the systems and methods described in the present disclosure provide an improvement over previous digital pathology analysis techniques and address a long-standing need for precise triaging in a quantitative manner, thereby improving patient outcomes.

In some other aspects, as described above, the disclosed systems and methods are capable of classifying digital pathology image data on the basis of cellular or tissue compartment type, such as by segmenting digital pathology images into epithelial, stromal, and other components. Advantageously, by segmenting digital pathology images in this way, the heterogeneity of the stroma can be examined using clustering algorithms, such that the tissue microenvironment components are further separated, segmented, or otherwise classified. As an example, the tissue microenvironment can be analyzed to further observe different constituent cells using unsupervised clustering. Furthermore, quantitative analyses can be carried out on the clustered data in order to characterize the tissue specimen to assist in the recognition of disease. For example, the inertia of the data clusters can be computed and used as a quantitative marker for characterizing the tissue specimen. In some embodiments, a report can be generated that may include an indication categorizing breast cancer by the combined effects of stromal and epithelial inertia.

For example, embodiments of the present disclosure include analysis of breast tissue microarrays and surgical specimens to identify different cell signatures in the tumor and its microenvironment using both unsupervised and supervised strategies. In certain embodiments, a deep learning model is built to separate the epithelial, stromal, and other cellular components of the tissue. This allows for precise investigation of different cellular distributions and their features in each of these components. Further embodiments include evaluation of the epithelial and stromal regions as indicators of cancer.

In some embodiments, the deep learning model implemented to analyze the digital pathology image data can be a deep neural network. For example, the deep neural network can be a convolutional neural network. In general, the deep learning model (e.g., convolutional neural network, deep neural network, or other deep learning model) is trained on training data to identify epithelial breast cells from their microenvironment.

The systems and methods described in the present disclosure can provide advantages for the analysis of digital pathology images in the healthcare setting by improving risk stratification as well as early detection. For example, the disclosed systems and methods are capable of generating classified feature data and/or reports indicating quantitative characterization of tissue specimens based on the application of digital pathology images to a deep learning model. These outputs assist clinicians in their diagnosis, thereby enabling faster and more reliable patient care. As one non-limiting example, digital pathology images can be analyzed using a machine learning framework in order to identify spatial characteristics of early stage disease (e.g., DCIS) that can help in triaging breast biopsies for better patient outcomes.

Referring now to FIG. 1, a flowchart is illustrated as setting forth the steps of an example method for generating classified feature data from digital pathology image data using a suitably trained neural network or other machine learning algorithm, where the classified feature data indicate a classification of pixels and/or regions in the digital pathology image data into various different classes.

The method includes accessing digital pathology image data with a computer system, as indicated at step 102. Accessing the digital pathology image data may include retrieving such data from a memory or other suitable data storage device or medium. Alternatively, accessing the digital pathology image data may include acquiring such data with an imaging system (e.g., a digital slide scanning system) and transferring or otherwise communicating the data to the computer system, which may be a part of the imaging system. In general, the digital pathology image data can include digital pathology images, such as digital images of tissue specimens obtained from a biopsy, surgical specimen, tissue microarray, or the like. In some instances, the digital pathology image data can include digital images of H&E stained slides.

A trained neural network (or other suitable machine learning algorithm) is then accessed with the computer system, as indicated at step 104. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In general, the neural network is trained, or has been trained, on training data in order to classify pixels and/or regions within digital pathology image data. For example, the neural network can be trained to classify pixels and/or regions within a digital pathology image of a breast tissue biopsy as belonging to classes indicating breast cancer and/or distinguishing between different high-risk breast lesions. As another example, the neural network can be trained to classify pixels and/or regions within a digital pathology image of a breast tissue biopsy as belonging to different cell types (e.g., epithelial cells, stromal cells).

In some instances, more than one trained neural network may be accessed. For example, a first neural network may have been trained on first training data to generate a first feature map and a second neural network may have been trained on second training data to generate a second feature map that is different from the first feature map. As an example, the first feature map may be associated with different pathology classes (e.g., DCIS, benign, UDH, ADH), whereas the second feature map may be associated with different cell type classes (e.g., epithelial, stromal).

As described below, the deep neural network can implement any suitable neural network architecture. For example, the deep neural network could implement a convolutional neural network, a residual neural network, or the like. Alternatively, the neural network(s) could be replaced with other suitable machine learning algorithms, such as those based on supervised learning, unsupervised learning, deep learning, ensemble learning, dimensionality reduction, and so on. As non-limiting examples, the deep neural network can implement a ResNet architecture, a ResNet50 architecture, a VGG16 architecture, a VGG19 architecture, an InceptionResNetV2 architecture, or the like.

In some instances, transfer learning can be used to re-train or otherwise adjust the trained neural network that has been accessed by the computer system. For example, the trained neural network may be a pretrained VGG16 model (or other suitable deep neural network model), which can be modified and retrained for classifying the digital pathology image data.

The digital pathology image data are then input to the one or more trained neural networks, generating output as classified feature data, as indicated at step 106. For example, the classified feature data may include feature maps associated with different classes (e.g., different pathology classes, different cell type classes). The feature maps may depict the spatial distribution or spatial patterns of features, statistics, or other parameters associated with the different classes.

As one example, the feature maps may indicate the local probability for a particular classification (i.e., the probability that a pixel belongs to a particular class), such as DCIS, benign lesion, UDH, ADH, epithelial cells, stromal cells, and the like.

As another example, the feature maps may indicate a classification of the input digital pathology image data (e.g., by assigning a particular classification to each pixel in the feature map). For instance, the trained neural networks may be trained to implement automatic pattern recognition to generate feature maps that classify pathology type and/or cell type on digital pathology images.

As described, the goal of the deep neural network model is to classify large tissue slides into different classes (e.g., different pathology classes, different cell type classes). Thus, each tile will be associated to one of the learned classes and a global matrix of classes can be obtained for the entire slide, where each position in the matrix corresponds to a tile from the image. To achieve this, the following competing constraints are considered: while the size of the tile should be large enough to contain meaningful information it should also be as small as possible to make the overall tissue image mask look less rasterized and able to delineate borders between classes. To balance these constraints, the tiles can be resized (e.g., to a smaller 48×48 size).

In one example, the computer system (e.g., computing device 1550, server 1552) accesses a deep neural network in step 104 and applies the digital pathology image data to the deep neural network in step 106. The deep neural network generally includes an input layer, one or more hidden layers or nodes, and an output layer. Typically, the input layer includes as many nodes as inputs provided to the computer system. The number, and the type, of inputs provided to the computer system may vary based on the particular task for the deep neural network. Accordingly, the input layer of the artificial neural network may have a different number of nodes based on the particular task for the deep neural network.

The input layer connects to the one or more hidden layers. The number of hidden layers varies and may depend on the particular classification task. Additionally, each hidden layer may have a different number of nodes and may be connected to the next layer differently. For example, each node of the input layer may be connected to each node of the first hidden layer. The connection between each node of the input layer and each node of the first hidden layer may be assigned a weight parameter. Additionally, each node of the deep neural network may also be assigned a bias value. However, each node of the first hidden layer may not be connected to each node of the second hidden layer. That is, there may be some nodes of the first hidden layer that are not connected to all of the nodes of the second hidden layer. The connections between the nodes of the first hidden layers and the second hidden layers are each assigned different weight parameters. Each node of the hidden layer is associated with an activation function. The activation function defines how the hidden layer is to process the input received from the input layer or from a previous input or hidden layer. These activation functions may vary and be based on not only the type of classification task, but may also vary based on the specific type of hidden layer implemented.

Each hidden layer may perform a different function. For example, some hidden layers can be convolutional hidden layers which can, in some instances, reduce the dimensionality of the inputs, while other hidden layers can perform more statistical functions such as max pooling, which may reduce a group of inputs to the maximum value, an averaging layer, among others. In some of the hidden layers, each node may be connected to each node of the next hidden layer. Some neural networks including more than, for example, three hidden layers may be considered deep neural networks.

The last hidden layer in the deep neural network is connected to the output layer. Similar to the input layer, the output layer typically has the same number of nodes as the possible outputs. In an example in which the deep neural network is a multiclass classifier, the output layer may include, for example, a number of different nodes, where each different node corresponds to a different class or label of the digital pathology image data. A first node may indicate that certain pixels in the digital pathology image data are classified as a normal (or benign) class type, a second node may indicate that certain pixels in the digital pathology image data are classified as a DCIS class type, and a third node may indicate that certain pixels in the digital pathology image data are classified as a stroma class type. Additionally or alternatively, an additional node may indicate that certain pixels in the digital pathology image data correspond to an unknown (or unidentifiable) class. In some embodiments, the computer system then selects the output node with the highest value and indicates to the computer system or to the user the corresponding classification of the digital pathology image data (e.g., by outputting and/or displaying the classified feature data). In some embodiments, the computer system may also select more than one output node.

Figure 2:
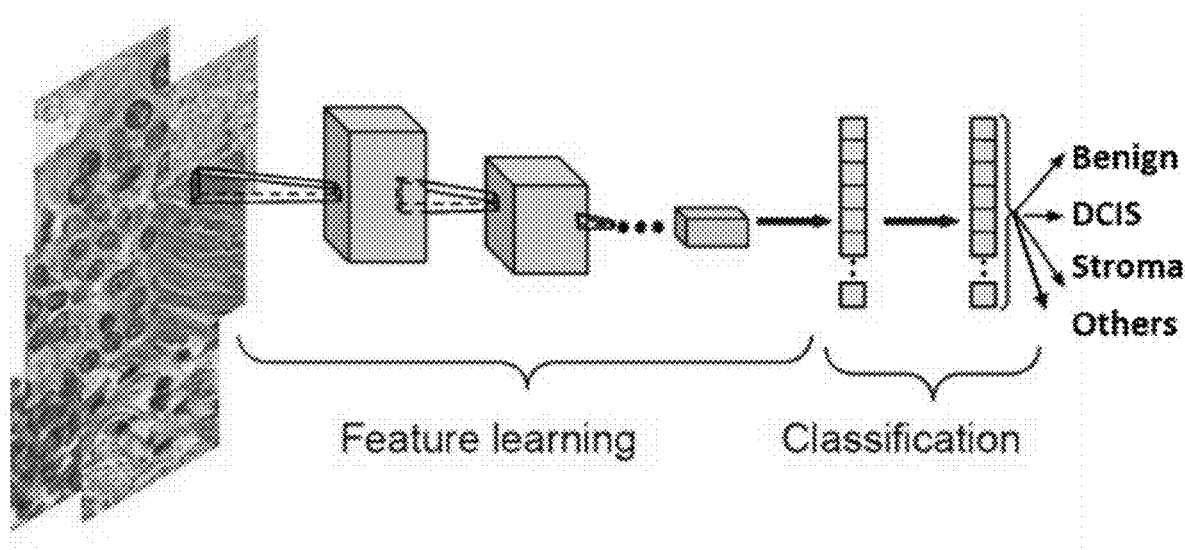
FIG. 2 illustrates an example neural network architecture for classifying digital pathology image data based on a pathology class type.

Referring to FIG. 2, in some embodiments the deep neural network can be configured to generate classified feature data as digital pathology image data that have been classified into different pathology class types. In this example, a pretrained VGG16 neural network was modified and retrained for classifying the digital pathology image data. After inspecting the model accuracies, hyperparameters like the type of optimizer to minimize loss function, mini batch size, number of epochs, learning rate and regularization factor can be optimized for the classification task. After achieving the desired accuracy, the final neural network model can be projected on large patient areas to validate the spatial performance of the neural network model.

Figure 3D:
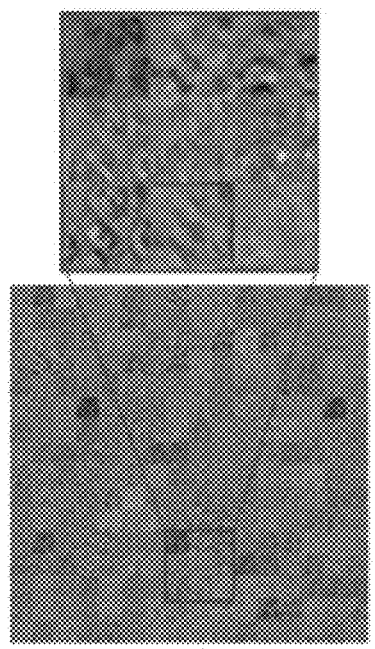
FIG. 3A-3D show examples of features extracted by the neural network of FIG. 2 using the H&E stained images in accordance with an embodiment of the present disclosure. Features extracted by layer 2 in FIG. 3B, layer 7 in FIG. 3C, and layer 19 in FIG. 3D.
Figure 3C:
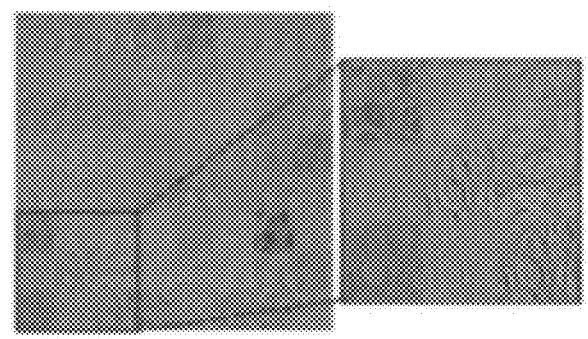
Figure 3B:
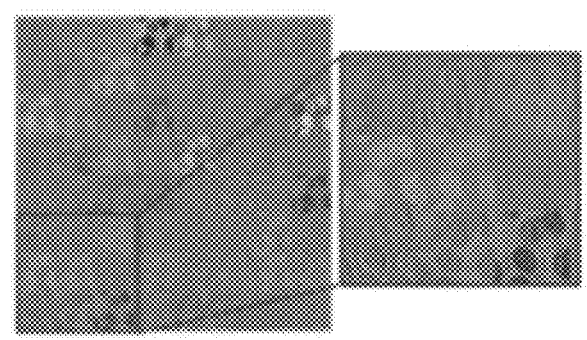
Figure 3A:
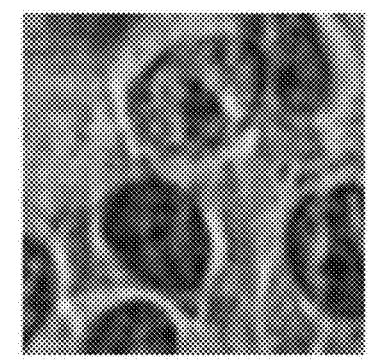

FIGS. 3A-3D show example features that are extracted by different layers of the deep neural network. In this example, the input digital pathology image data includes an H&E stained image, shown in FIG. 3A. FIG. 3B shows the features from layer 2 (i.e., the first convolutional layer) of a 41-layer deep neural network, FIG. 3C shows the features from layer 7 (i.e., the third convolutional layer) of the 41-layer deep neural network, and FIG. 3D shows the features from layer 19 (i.e., the eighth convolutional layer) of the 41-layer deep neural network. As the layer number increases, the complexity of the derived features increases. In the initial layers, the deep neural network primarily extracts the outer edges of the nuclei and in the subsequent layers the deep neural network estimates the finer edges in the nucleoli and the stromal fibers interspersed in the epithelial nuclei. In summary, the deep neural network is automatically segmenting the nuclei and extracting different nuclear features for the classification task.

In a non-limiting example, the neural network model is capable of achieving accuracies in the different phases of model development as shown below in Table 1.

TABLE 1

| Model Accuracies in the Training, Calibration (Tuning), and Validation Phases | |
|---|---|
| Training | 91.07% (calculated on ~22,000 images to develop the model) |
| Calibration | 90.98% (calculated on ~8,800 images to tune the model) |
| Validation | 88.67% (calculated on ~8,800 images from different patients that were not part of the model) |

High accuracy of about 89% (about 20-40% higher than current standards and reports) in the independent validation step indicates that the model is generalizable and translatable to a large variety of patient samples. As described above, the neural network model can be used to classify different lesions and can identify areas of DCIS and separates them from the benign population (normal+UDH+ADH).

FIGS. 4A and 4B illustrate example digital pathology image data (FIG. 4A) and the resulting classified feature data (FIG. 4B) generated by applying that digital pathology image data to a deep learning model, such as a the deep neural network of FIG. 2. The relevant features extracted by the deep learning model enable classifying image patches into different classes as shown in FIG. 4B. In the illustrated example, the deep learning model was capable of identifying areas of DCIS and separating them from the benign population (normal+UDH+ADH).

Thus, in some embodiments, the disclosed systems and methods can be of interest to both healthcare clinics for risk stratification as well as early detection and the traditional digital pathology companies to add to their digital pathology suite of programs. Upwards of a million biopsy samples are done annually, which can be analyzed using the disclosed systems and methods in order to provide precise stratification of intraductal lesions, for example, which can help overcome the problem of under/over diagnoses associated with these lesions. Additionally or alternatively, the systems and methods described in the present disclosure can also assist pathologists in borderline cases or differential diagnoses, such as high-grade hyperplasia and low-grade DCIS.

Figure 5:
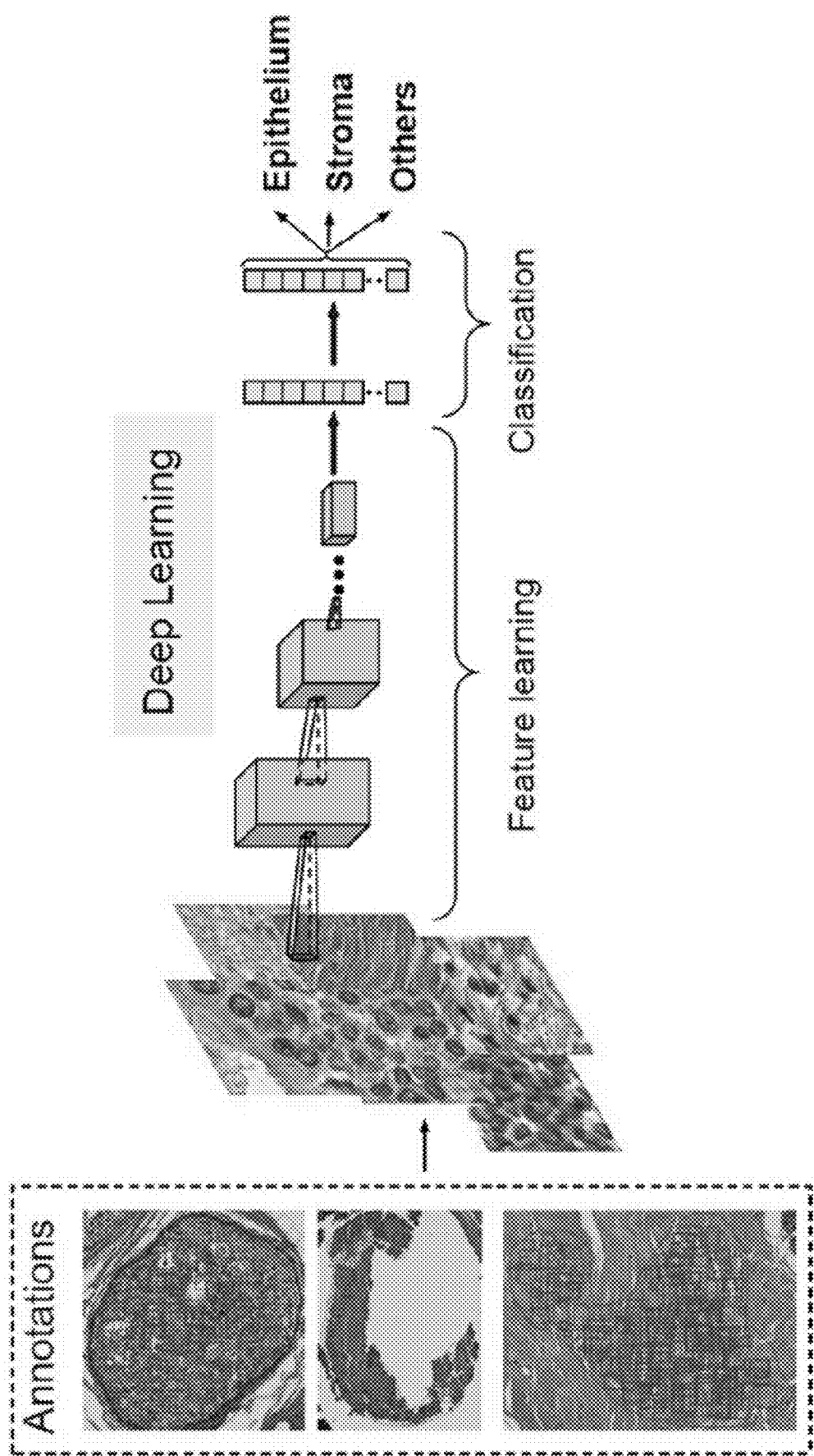
FIG. 5 illustrates an example neural network architecture for classifying digital pathology image data based on a cellular compartment type.
Figure 6:
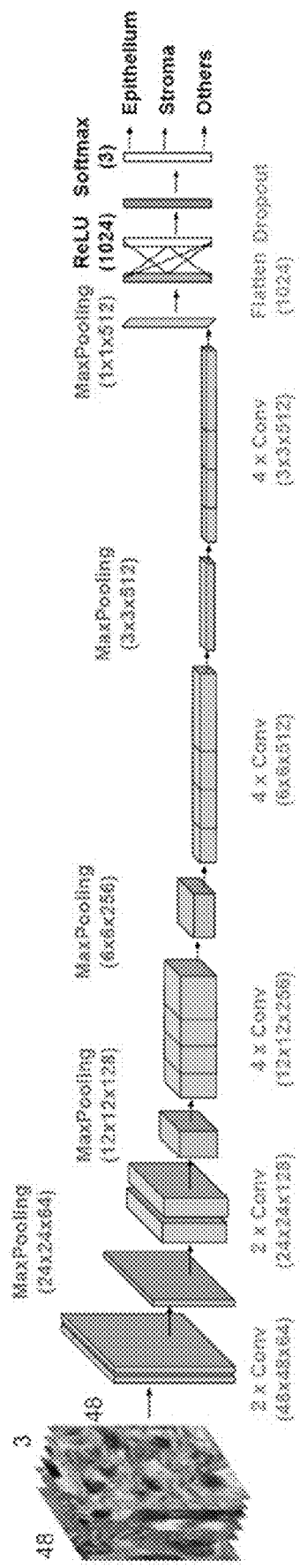
FIG. 6 shows an example neural network architecture in accordance with an embodiment of the present disclosure. VGG19 is used for transfer learning. Parameter values are given in parenthesis.

Referring to FIGS. 5 and 6, in some embodiments the deep neural network can be configured to generate classified feature data as digital pathology image data that have been classified into cell types, or compartments. For instance, the classified feature data may be digital pathology image data that have been segmented into different cell or tissue compartments. In this example, a VGG19 neural network was implemented. In the illustrated embodiment, the VGG19 neural network has a sequence of several layers that perform convolution (with the given kernel size and number of filters) and max-pooling for down sampling (with the specified filter size and stride). They are followed by a layer that flattens its output volume into a vector to be used as input for the subsequent fully connected layers. A dense layer with a Rectified Linear Unit ("ReLU") activation function with 1,024 units is also included in the network, followed by a dropout layer with the aim to improve the generalization ability, and consequently decrease overfitting. Finally, a dense layer with a softmax activation function gives the n-dimensional output of the network, given in the form of probabilities of belonging to each class, where n is the number of classes (e.g., three in the illustrated embodiment). In some implementations, a batch size of 32 images is considered.

The weights of the initial layers are preserved (e.g., frozen) from a pre-trained network as they refer to general feature information obtained from learning over a large database. A number of trainable end layers that is appropriate for learning H&E images can be searched for. As a non-limiting example, the optimal number of trainable end layers can be 12. In other implementations, a different number of trainable end layers may also be used.

The optimizer to be used for weight adjustment, when minimizing the difference between the predicted output and the ground truth, is another parameter that can be searched for or otherwise determined for an appropriate solution. In a non-limiting example, a learning rate of $1 \times 10^{-7}$ without a decay can be used. The dropout rate for the dropout layer, which gives the percent of units that are blocked, can also be tuned. As a non-limiting example, the dropout rate can be tuned to a value of 0.2.

Based on the information about general tissue architecture, there may be some instances where scarce tiles belonging to one class will have a neighborhood of other classes. For instance, it is uncommon that a few isolated pixels of epithelium will be surrounded by stroma as epithelial cells are present in ducts or lobules. Therefore, a substantial number of pixels from one class would be present next to an appreciable number of pixels from another, especially in the case of epithelium and stroma. In some embodiments, a majority filter can be applied to the classified images to remove classification noise.

Referring again to FIG. 1, the classified feature data generated by inputting the digital pathology image data to the trained neural network(s) can then be displayed to a user, stored for later use or further processing, or both, as indicated at step 108.

As described below, in some embodiments the classified feature data can be further analyzed to examine the heterogeneity in the tissue microenvironment. For example, in some instances the classified feature data can indicate segmented digital pathology image data in which the digital pathology image data are separated between components such as epithelium, stroma, and other cellular components. An, unsupervised segmentation can then be applied to both the epithelial and stromal compartments to further analyze these components in relation to disease. For example, a K-means clustering operation can be applied for the pixel values of each component in order to distinguish between regions in the image(s) that belong to different disease states and the type of cellular moieties present around them. A more detailed discussion of these embodiments is provided below with respect to FIG. 8.

Figure 7:
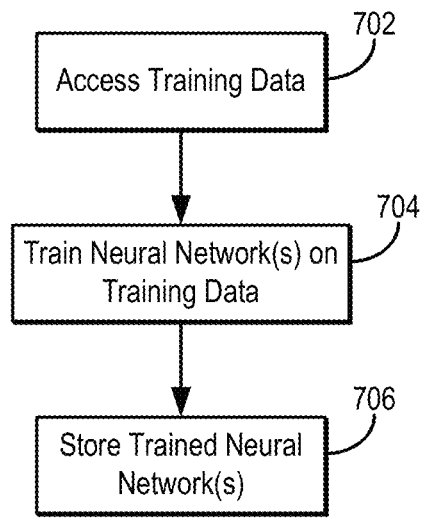
FIG. 7 is a flowchart setting forth the steps of an example method for training a deep learning model, such as a neural network, to classify digital pathology image data.

Referring now to FIG. 7, a flowchart is illustrated as setting forth the steps of an example method for training one or more neural networks (or other suitable machine learning algorithms) on training data, such that the one or more neural networks are trained to receive input as digital pathology image data in order to generate output as classified feature data, which may include digital pathology image data whose pixels have been assigned a class or otherwise classified as belonging to different class types, such as pathology class types and/or cell (or tissue compartment) class types.

In general, the neural network(s) can implement any number of different neural network architectures. For instance, the neural network(s) could implement a convolutional neural network, a residual neural network, or the like. In some instances, the neural network(s) may implement deep learning.

Alternatively, the neural network(s) could be replaced with other suitable machine learning algorithms, such as those based on supervised learning, unsupervised learning, deep learning, ensemble learning, dimensionality reduction, and so on.

The method includes accessing training data with a computer system, as indicated at step 702. Accessing the training data may include retrieving such data from a memory or other suitable data storage device or medium. Alternatively, accessing the training data may include acquiring such data with an imaging system (e.g., by scanning pathology slides with a digital slide scanner) and transferring or otherwise communicating the data to the computer system, which may be a part of the imaging system.

Additionally or alternatively, the method can include assembling training data from digital pathology image data using a computer system. This step may include assembling the digital pathology image data into an appropriate data structure on which the machine learning algorithm can be trained. Assembling the training data may include assembling digital pathology image data, segmented digital pathology image data, and other relevant data. For instance, assembling the training data may include generating labeled (or annotated) data and including the labeled data in the training data. Labeled data may include digital pathology image data, segmented digital pathology image data, or other relevant data that have been labeled as belonging to, or otherwise being associated with, one or more different classifications or categories. For instance, labeled data may include digital pathology image data and/or segmented digital pathology image data that have been labeled based on pathology classes (e.g., normal, benign, UDH, ADH, DCIS), cell type (e.g. epithelial, stromal), or the like. The labeled data may include labeling all data within a field-of-view of the digital pathology image data and/or segmented digital pathology image data, or may include labeling only those data in one or more regions-of-interest within the digital pathology image data and/or segmented digital pathology image data. The labeled data may include data that are classified on a pixel-by-pixel basis, or a regional or larger volume basis.

In general, the training data can include digital pathology images, such as hematoxylin and eosin ("H&E") stained images. The digital pathology images used in the training data can include images from specimens encompassing various different pathology and/or cell type classes. For example, the digital pathology images can depict specimens including pathology classes such as normal breast tissue, usual hyperplasia, atypical hyperplasia columnar change, atypical hyperplasia without columnar change, ductal carcinoma in-situ, and the like. Additionally or alternatively, the digital pathology images can depict specimens including cell types such as epithelial cells, stromal cells, and the like.

In one example study, a total of 20,708 digital pathology images (e.g., H&E slide images) were curated for training, 8,876 images for calibration, and 8,833 images for independent validation. In another example study, images of whole H&E slides, each corresponding to a different patient, were acquired. The H&E stains can be used to identify the morphological changes associated with cancer development and its subsequent progression. Some regions of the H&E images can be labeled (i.e., annotated), such as regions from each image that correspond to one of the following classes: epithelium (normal, malignant, DCIS), dense stroma, reactive stroma, and the rest in a class that is further referred as "others." Each contour can be chosen to be specific to its class and its size can vary from very small regions having an area of <1 mm×1 mm up to large regions with areas of about 1.5 mm×1.5 mm. Each annotated contour is used to create image tiles that are assembled in the training data, which may also include assembling some image tiles for validation and test sets.

In some embodiments, squared tiles varying in size from 48×48 pixels up to 256×256 pixels are cropped from each annotated section. The sizes of the tiles can be randomly generated within the mentioned bounds. Random sizes for the cropped images can be considered with the goal of feeding the deep neural network model with sections that contain multiple views of the tissue, from capturing minor details in the smallest squared image to having an overview in the largest squared tile case. The positions of the cropped images are randomly generated such that they lie entirely inside the contour.

All the tiles can be resized to the minimal size of 48×48 pixels when they are applied to the deep neural network model. A filter can also be applied to remove tiles with minimal tissue from the training data. For example, if background accounts for more than 30% of the tile area, then the image tile is not passed to the model. The number of tiles that are cropped from each annotated contour is proportional to the area of the annotation; that is, the larger the initial area, the more patches are selected. In some implementations, the number of tiles per annotation can be limited, such as to no more than 100 tiles per annotation.

The actual number of tiles can be obtained by dividing the area of the annotated region to the area of a tile with a side equal to the average size (e.g., the mean between the minimum and maximum, which is 152 when the minimum is 48 and the maximum is 256). The double of this division result represents the number of tiles selected for the annotated area. This ensures that a large part of the contour is cropped with overlapping tiles. Also, distinct patients can be used for training, validation, and test sets for robust classification and unbiased estimates.

One or more neural networks (or other suitable machine learning algorithms) are trained on the training data, as indicated at step 704. In general, the neural network can be trained by optimizing network parameters (e.g., weights, biases, or both) based on minimizing a loss function. As one non-limiting example, the loss function may be a mean squared error loss function.

Training a neural network may include initializing the neural network, such as by computing, estimating, or otherwise selecting initial network parameters (e.g., weights, biases, or both). Training data can then be input to the initialized neural network, generating output as classified feature data. The quality of the classified feature data can then be evaluated, such as by passing the classified feature data to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network. Different types of training algorithms can be used to adjust the bias values and the weights of the node connections based on the training examples. The training algorithms may include, for example, gradient descent, Newton's method, conjugate gradient, quasi-Newton, Levenberg-Marquardt, among others.

The one or more trained neural networks are then stored for later use, as indicated at step 706. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

In some embodiments, the classified feature data generated using the systems and methods described in the present disclosure can be further analyzed to generate a report indicating different aspects or characteristics of the analyzed tissue specimen. For example, the classified feature data may include segmented digital pathology image data, in which the digital pathology image data have been segmented or otherwise separated into different tissue compartments (e.g., into the epithelial and stromal compartments). These different tissue compartments can then be analyzed for diagnostic and/or prognostic information.

Current histopathological diagnosis involves human expert interpretation of stained images for diagnosis. This process is prone to inter-observer variability, often leading to low concordance rates amongst pathologists across many types of tissues. Further, since structural features are mostly just defined for epithelial alterations during tumor progression, the use of associated stromal changes is limited.

Advantageously, the systems and methods described in the present disclosure enable analysis of digital pathology images to provide precise and quantitative metrics of disease from both epithelial and stromal cells. Embodiments of the present disclosure include a convolutional neural network approach to identify epithelial breast cells from their microenvironment (e.g., using the method described above with respect to FIG. 1). Further embodiments include analyzing the microenvironment to further observe different constituent cells using unsupervised clustering. Further embodiments include, categorizing breast cancer by the combined effects of stromal and epithelial inertia. Together, the systems and methods provide insight and evidence of cancer association for interpretable features from deep learning methods that provide improved opportunities for comprehensive analysis of standard pathology images.

Figure 8:
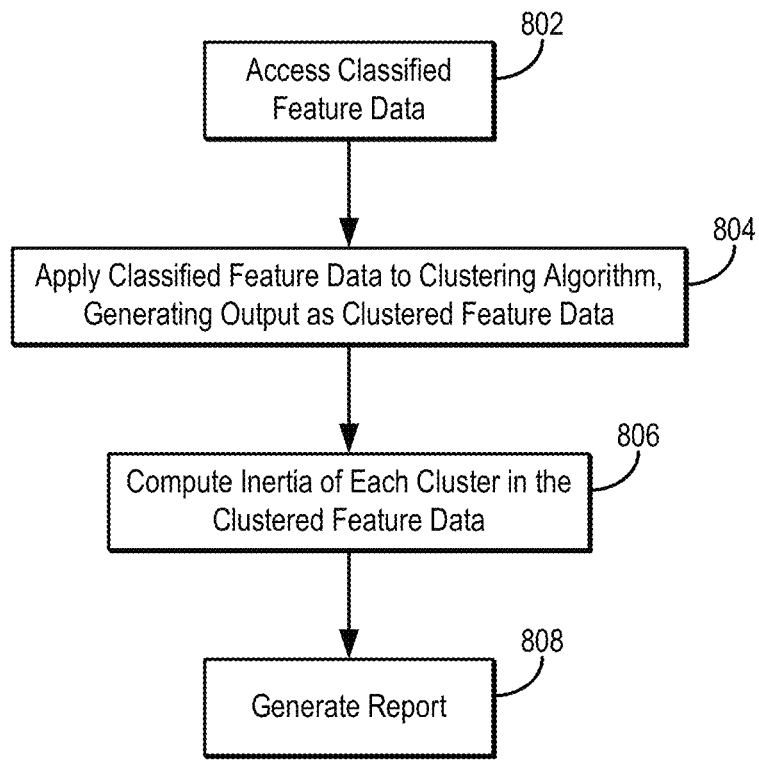
FIG. 8 is a flowchart setting forth the steps of an example method for generating a report that characterizes a tissue based on a quantitative analysis of spatial feature data (e.g., inertia) computed from clusters of classified feature data (e.g., segmented epithelial and stromal compartments).

Referring now to FIG. 8, a flowchart is illustrated as setting forth the steps of an example method for generating a report that indicates a characterization of the tissue microenvironment based on clustering the classified feature data and computing quantitative parameters of the resulting clustered feature data.

The method includes accessing classified feature data with a computer system, as indicated at step 802. In general, the classified feature data have been generated from digital pathology image data, such as according to the method described above with respect to FIG. 1. As such, the classified feature data may indicate classifications of digital pathology image data into various classes, such as different pathology classes (e.g., normal, benign, UDH, ADH, DCIS), different cell type classes (e.g., epithelial, stromal, other), other suitable classifications of digital pathology images, and/or combinations thereof.

Accessing the classified feature data may include retrieving such data from a memory or other suitable data storage device or medium. Alternatively, accessing the classified feature data may include generating such data with the computer system (e.g., by implementing the method described above with respect to FIG. 1).

The classified feature data are then applied to a clustering algorithm using the computer system, generating output as clustered feature data, as indicated at step 804. Furthermore, in some embodiments the clustered feature data can be applied to one or more additional iterations, repetitions, or applications of a clustering algorithm. For example, in order to increase the sensitivity of the model, the classified feature data can be applied to a first clustering algorithm configured for a first number of clusters, generating output as first clustered feature data. The first clustered feature data can then be applied to a second clustering algorithm (which may be the same type of clustering algorithm as the first clustering algorithm, or may be a different type of clustering algorithm) configured for a second number of clusters (which may be the same number of clusters as the first number of clusters, or may be a different number of clusters), generating output as second clustered feature data. As a non-limiting example, a K-means clustering algorithm with two clusters is first applied to further filter out small regions that were misclassified by the deep neural network model to only analyze patterns within one cell type at a time. Each detected component is then subsequently subject to another K-means clustering algorithm using various number of clusters ranging between two and five, for example.

To measure if there are significant differences between various cluster distributions of each class and how that correlates to distinct disease stages over multiple patients, an inertia parameter can be computed for each cluster in the clustered feature data, as indicated at step 808. For example, inertia of both the epithelial and stromal clusters can be computed. In general, the inertia parameter measures the dispersion of points within a cluster by computing the sum of squared distances for each point in the cluster to its assigned cluster centroid.

A report that indicates a characterization of the tissue microenvironment for the tissue specimen depicted in the digital pathology image data is then generated by the computer system, as indicated at step 810. In general, the generated report is based on the computed inertia parameters for each cluster in the clustered feature data. Alternatively, the generated report may also be based on the clustered feature data, the classified feature data, the digital pathology image data, or other relevant data. In some embodiments, the generated report can indicate inertia parameters individually (e.g., inertia parameters computed for clusters in the epithelium separate from inertia parameters computed for clusters in the stroma). In some other embodiments, the generated report can indicate inertia parameters analyzed in combination (e.g., combined analysis of inertia computed from epithelium and inertia computed from stroma).

Figure 9:
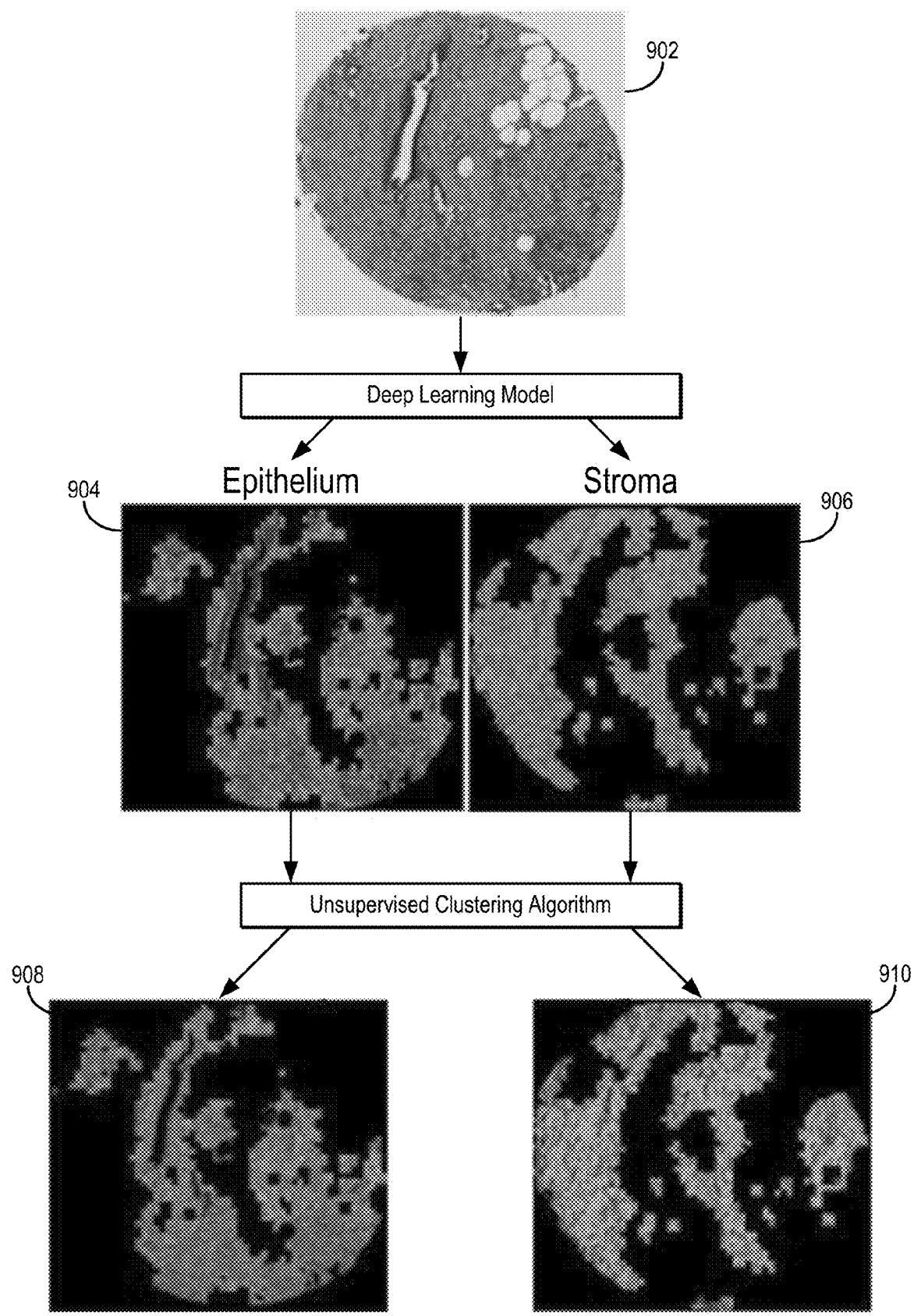
FIG. 9 is an example workflow for segmenting digital pathology images into epithelial and stromal compartments and clustering those compartments in order to analyze the tissue microenvironments.

An example workflow for generating a report that indicates a quantification or characterization of tissue microenvironment for a tissue specimen is shown in FIG. 9. In the illustrated embodiment, a digital pathology image 902 of a tissue specimen is applied to a deep learning model, generating output as classified feature data. In this example, the classified feature data include a first feature map 904 that depicts segmented epithelium and a second feature map 906 that depicts segmented stroma. The digital pathology image 902 can be processed using the method described above with respect to FIG. 1 in order to generate these classified feature data, as an example. The classified feature data are then applied to an unsupervised clustering algorithm, generating output as clustered feature data. In this example, the clustered feature data can include a first cluster map 908 that depicts clusters of data in the first feature map 904 and a second cluster map 910 that depicts clusters of data in the second feature map 906. The clustered feature data can be generated using the method described above with respect to FIG. 8, as an example. As described above, the clustered feature data can then be processed to compute quantitative parameters, such as the inertia of clusters in the first and second cluster maps 908, 910.

In some embodiments, the digital pathology image data can be normalized before applying the image data to the neural network. For example, after accessing the digital pathology image data with a computer system (e.g., in step 102 in FIG. 1), the digital pathology image data can be normalized for sample preparation, imaging, and/or specimen handling variations across clinical labs or other sites where tissue samples are collected and imaged to generate digital pathology image data. The normalized digital pathology image data can then be applied to one or more neural networks to generate classified feature data (e.g., in step 104 in FIG. 1), as described above. By normalizing the digital pathology image data for inter-clinical variations, the accuracy of the diagnostic model design can be improved.

Figure 10:
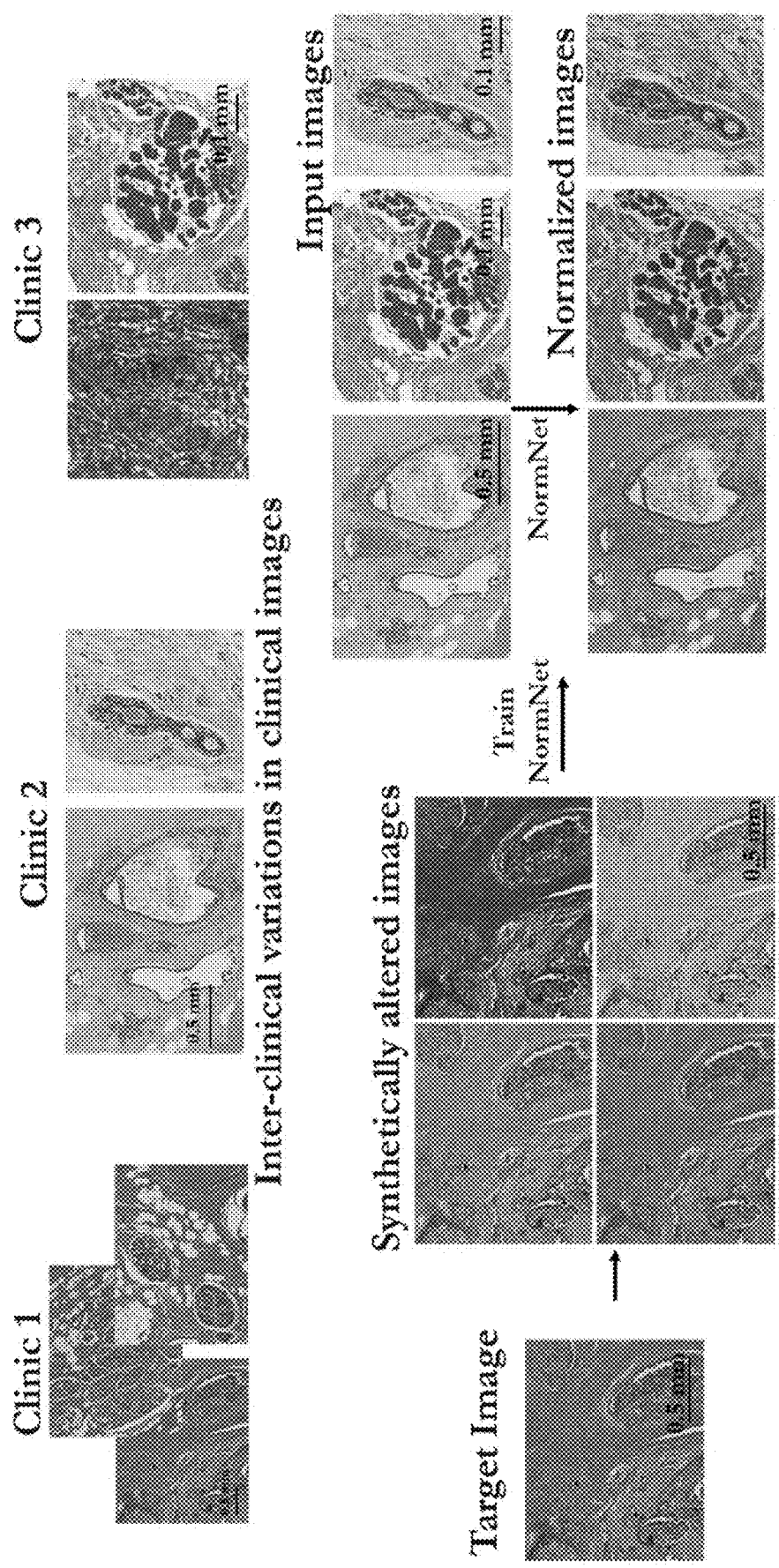
FIG. 10 illustrates an example process for normalizing digital pathology images for inter-clinical variations (e.g., variations in sample preparation, imaging, and/or specimen handling across different clinical sites) using a normalization network (e.g., a NormNet).

As one non-limiting example, the digital pathology image data can be normalized by applying the digital pathology image data to a neural network that has been trained to normalize images for inter-clinical variations (e.g., a NormNet). FIG. 10 illustrates an example workflow for implementing a NormNet to generate normalized digital pathology image data. In this example, digital pathology images obtained from three different clinical sites depict inter-clinical variations in the images, which may be attributable to different sample preparation techniques and/or protocols at the different clinical sites; different imaging techniques, equipment, and/or protocols at the different clinical sites; different specimen handling techniques and/or protocols at the different clinical sites; combinations thereof; and/or other inter-clinical variations.

A NormNet is trained on training data that can include digital pathology images that have been obtained from various different clinical sites. Additionally or alternatively, the training data may include digital pathology images obtained using various different sample preparations, imaging procedures, and/or specimen handling techniques. In some embodiments, the training data may also include digital pathology images that are augments to create synthetically altered images indicative of different sample preparations, imaging procedures, and/or specimen handling techniques. An example of such synthetic images is shown in FIG. 10. Digital pathology images can then be applied to a suitably trained normalization network, generating output as normalized digital pathology image data, as shown in FIG. 10. The normalized digital pathology image data include digital pathology images that have been normalized for inter-clinical variations, such as variations in sample preparation, imaging, and/or specimen handling.

In an example study, a tissue microarray containing 100 patient samples, each 1 mm in diameter, was obtained. The tissue microarray spanned a wide range of disease states including hyperplasia (20 cases), atypical hyperplasia (20), invasive (20 ductal and 20 lobular), and normal (20). Using a tissue microarray that spanned multiple different disease states allowed for a generalizable model development as it encapsulates a broad range of tumor and cell heterogeneity. The tissue microarray used in this example were formalin fixed and paraffin embedded and five microns thick samples. Multiple consecutive sections of the tissue microarray were used to stain for different molecular markers. In the example study, the digital pathology image data obtained included hematoxylin and eosin ("H&E") stained images. To take into account sample preparation and staining variability, some tissue sections were also obtained from a breast tissue registry. All the stained slides were scanned using a whole slide scanner.

Images of whole H&E slides, each corresponding to a different patient, were acquired. The H&E stains are used to identify the morphological changes associated with cancer development and its subsequent progression. The data set that was used for training the CNN architecture included a pathologist annotating some sections from each image that correspond to one of the following classes: epithelium (normal, malignant, DCIS), dense stroma, reactive stroma, and the rest in a class that is further referred as "others." Each contour was chosen to be specific to its class and its size varied from very small regions having an area of <1 mm×1 mm up to large ones with areas of about 1.5 mm×1.5 mm. There were 222 such contours annotated and each one of them was used to create image tiles that were used in the training, validation, and test sets of the CNN model. Squared tiles varying in size from 48×48 pixels up to 256×256 pixels were cropped from each annotated section. The sizes of the tiles are randomly generated within the mentioned bounds. Random sizes for the cropped images were considered with the aim of feeding the CNN model with sections that contain multiple views of the tissue, from capturing minor details in the smallest squared image to having an overview in the largest squared tile case. The positions of the cropped images were randomly generated such that they lie entirely inside the contour. All the tiles were resized to the minimal size of 48×48 pixels when they finally entered the CNN model.

Next, a filter was applied to remove tiles with minimal tissue. If the background contained more than 30% of the tile area, it was not passed to the model. The number of tiles that were cropped from each annotated contour is proportional to the area of the annotation: the larger the initial area, the more patches are selected, but no more than 100 tiles per annotation. The actual number of tiles was obtained by dividing the area of the annotated region to the area of a tile with a side of 152 (mean between the minimum 48 and the maximum 256); the double of this division result represents the number of tiles selected for the annotated area. This ensured that a large part of the contour is cropped with overlapping tiles.

Also, distinct patients were used for training, validation, and test sets for robust classification and unbiased estimates. There were 6 patients for training and 5 others for validation, the amount of tiles generated for the training set was 3,914 for the epithelial class, 2,578 for stroma, and 2,122 for others. For the validation set, 1,758 patches for epithelium, 1,114 for stroma and 414 for others are used. The test set is represented by an independent tissue microarray containing 100 patients.

The first step of the process for the H&E slides segmentation was the separation between components such as epithelium, stroma, and other cellular components. A CNN architecture was employed to achieve this delineation, such as by using the method described above with respect to FIG. 1. Next, unsupervised segmentation was applied to both the epithelial and stromal compartments for further investigation relating to disease. A K-means clustering operation was applied for the pixel values of each component, with the aim of distinguishing between regions in the image that belong to different disease states and the type of cellular moieties present around them. For example, the methods described above with respect to FIGS. 8 and 9 can be implemented.

The disclosed methods first precisely separate the tissue into the epithelial and stromal compartments for detailed analysis of each of these components for diagnostic or prognostic information. Therefore, the epithelial and stromal regions identified by the deep learning model discussed above were utilized. In order to increase the sensitivity of the model, a K-means approach with two clusters was applied to the result obtained to further filter out small regions that were misclassified by the CNN model to only analyze patterns within one cell type at a time. Each detected component was subsequently subject to another K-means clustering algorithm using various number of clusters ranging between 2 and 5. To measure if there were significant differences between various cluster distributions of each class and how that correlates to distinct disease stages over multiple patients, the inertia of both the epithelial and stromal clusters was computed. The inertia of a cluster measures the dispersion of points within the cluster by computing the sum of squared distances for each point to its assigned cluster centroid.

Figure 11A:
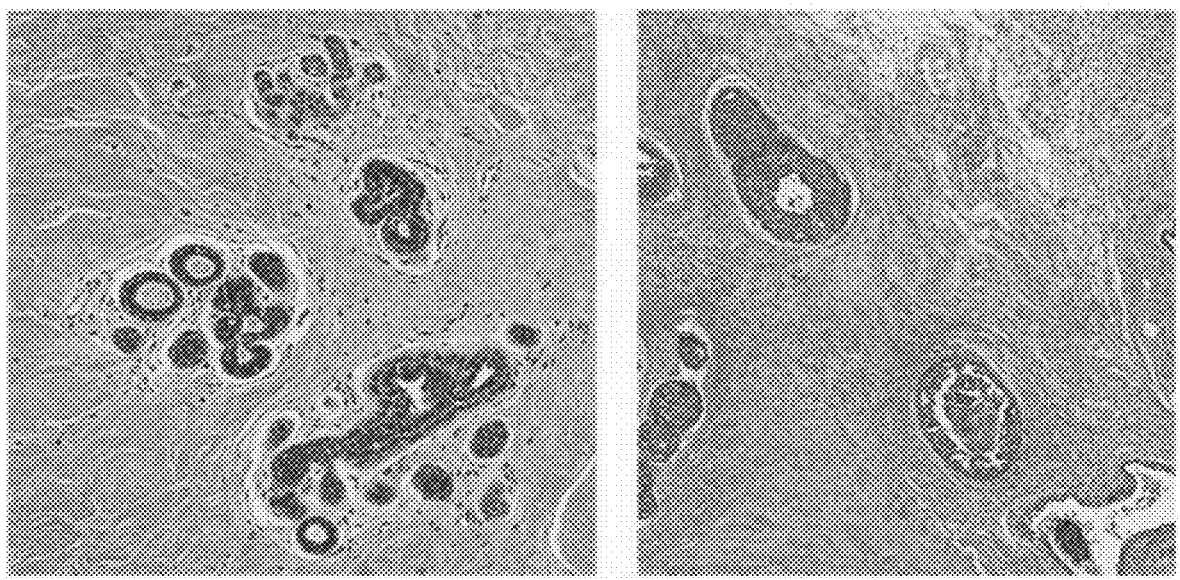
FIGS. 11A-11D illustrate classified feature data that depict a segmentation of a digital pathology image into various tissue compartments, and thus illustrate the performance of the developed deep learning strategy for identifying epithelial, stromal, and other cellular components (typically consisting of necrosis, red blood cells, secretions and mucin). In the illustrated example, a VGG19 classification network was applied to both surgical (training and validation) and tissue microarray (test) samples, which shows good correspondence with H&E images.
Figure 11B:
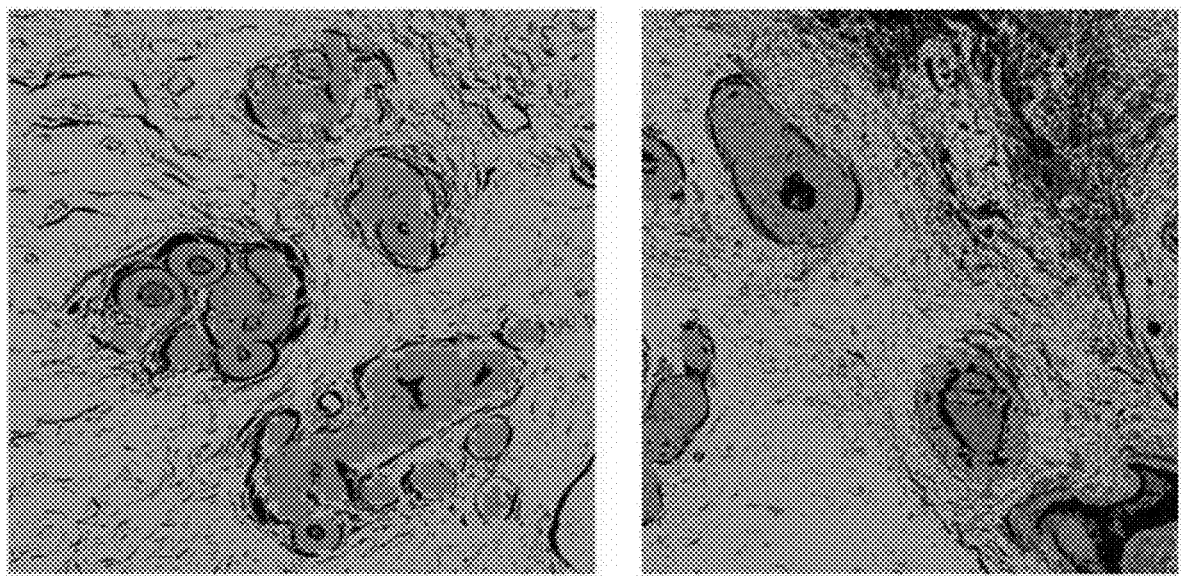
Figure 11C:
Figure 11D:
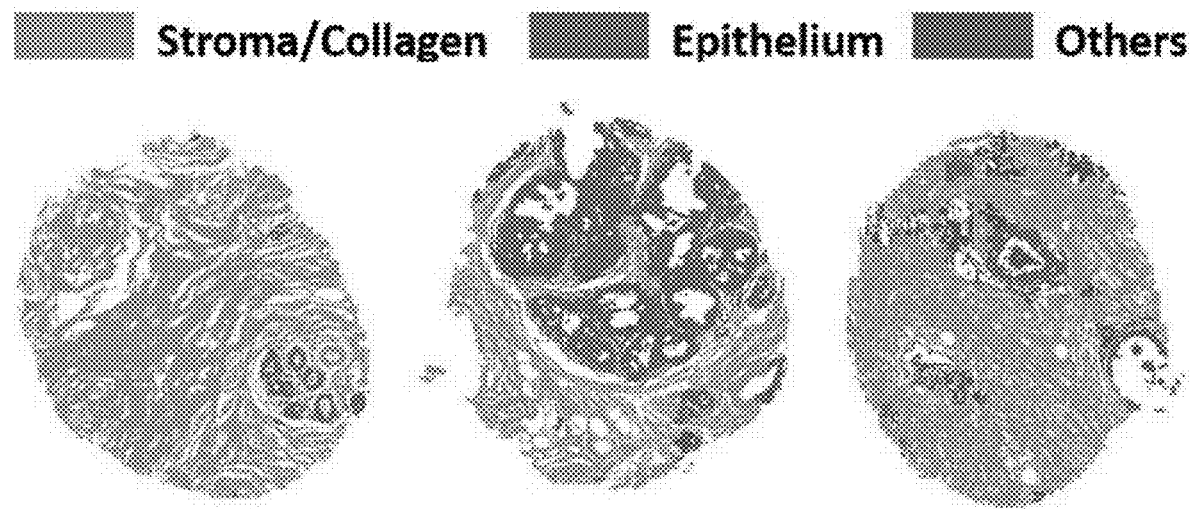

FIGS. 11A-11D illustrate classified feature data that depict a segmentation of a digital pathology image into various tissue compartments, and thus illustrate the performance of the developed deep learning strategy for identifying epithelial, stromal, and other cellular components (typically consisting of necrosis, red blood cells, secretions and mucin). In the illustrated example, a VGG19 classification network was applied to both surgical (training and validation) and tissue microarray (test) samples, which shows good correspondence with H&E images. FIG. 11A shows H&E stained images from two different surgical samples and FIG. 11B shows the resulting classified images generated by applying those H&E images to the deep learning model. FIG. 11C shows H&E stained images from the tissue microarray for three different patients with distinct disease states, and FIG. 11D shows the resulting classified images generated by applying those H&E images to the deep learning model.

In the illustrated example, a VGG19 classification network was selected because it allowed tiles of the smaller considered size, while preserving a high classification accuracy. FIG. 11B shows the classification performance on cropped regions from large surgical samples. Surgical resections represent a challenge in terms of size of the sample and data handling, but do provide unambiguous ground truth for disease that may not be present in limited sections from needle biopsies. High accuracy of tissue segmentation is evident by comparison with ground truth H&E stained images (FIG. 11A).

The example study also evaluated digital pathology image data obtained from a tissue microarray, which provides the opportunity for a large number of highly diverse samples but recognizes that the potential to examine many components of the tumor and microenvironment in each sample may be limited. FIGS. 11C and 11D illustrate the model performance on three samples from an independent tissue microarray containing 100 patients belonging to different disease states. This array was obtained from a different source to check for model robustness for samples processed and prepared in different institutions or settings. The model performs with similar accuracies on this external validation set. Each sample shown in FIG. 11D (classified images) and FIG. 11C (H&E stained images) belongs to a different patient. The results indicate a good agreement of the histologic units detected by the algorithm (FIG. 11D) with the ground truth (FIG. 11C).

Next, K-means images for the components identified by the CNN model were examined. The clustering algorithm was run for 300 iterations, 10 times with random seeds each time and the best solution was kept. The K-mean clustering algorithm was applied to the RGB values of the masked images based on the CNN results (i.e., the classified feature data corresponding to the different cellular components). The clustered images with 5 clusters were overlaid with grayscale H&E stained images to illustrate the class distributions along with a reference to the tissue architecture. Different colors in the overlaid images represent different clusters that are indicative of either different cellular types or subtypes within a cell type.

Figure 12A:
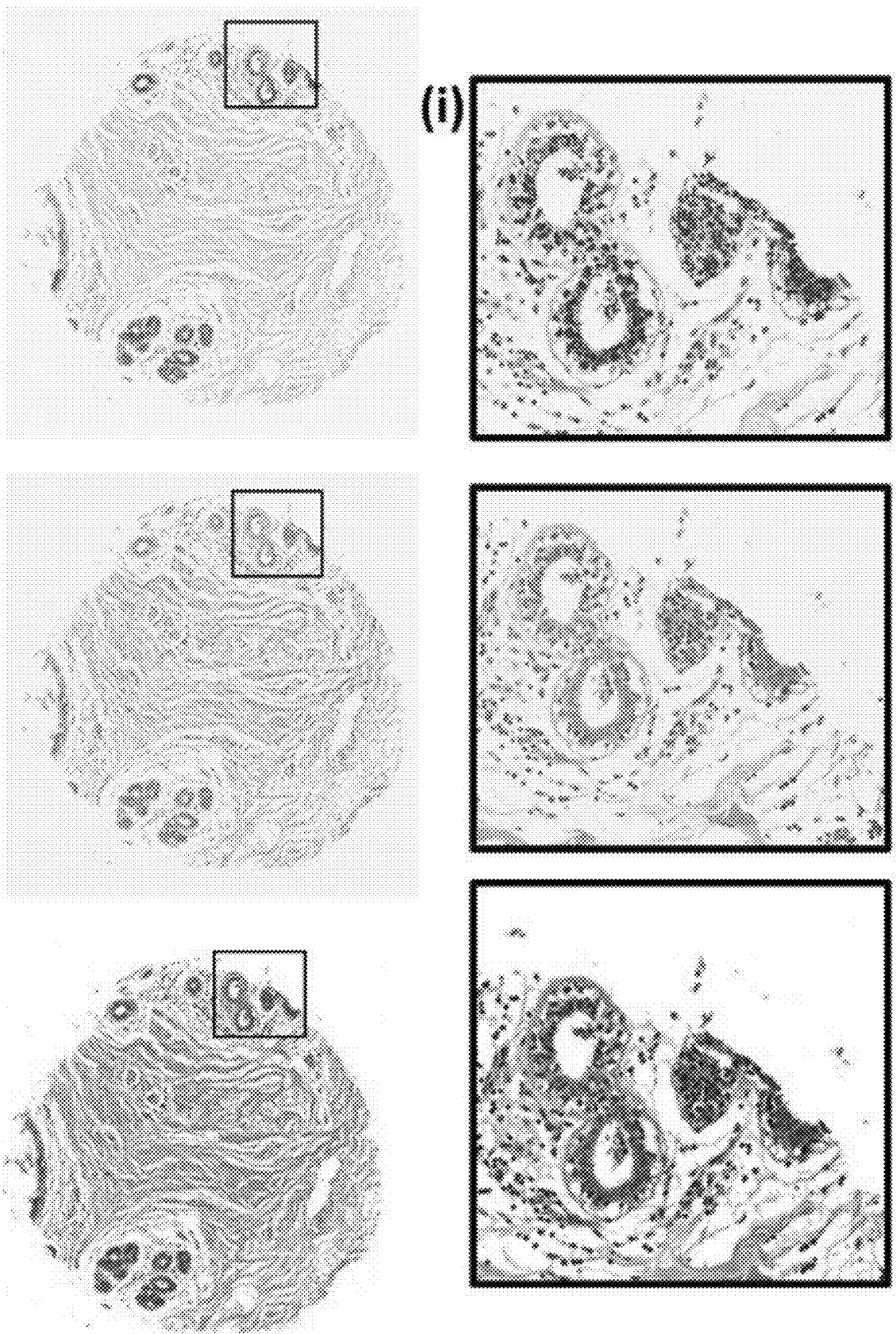
FIGS. 12A-12C show illustrate K-means clustering results overlaid on H&E stained images (gray scale) for test samples using five clusters.
Figure 12B:
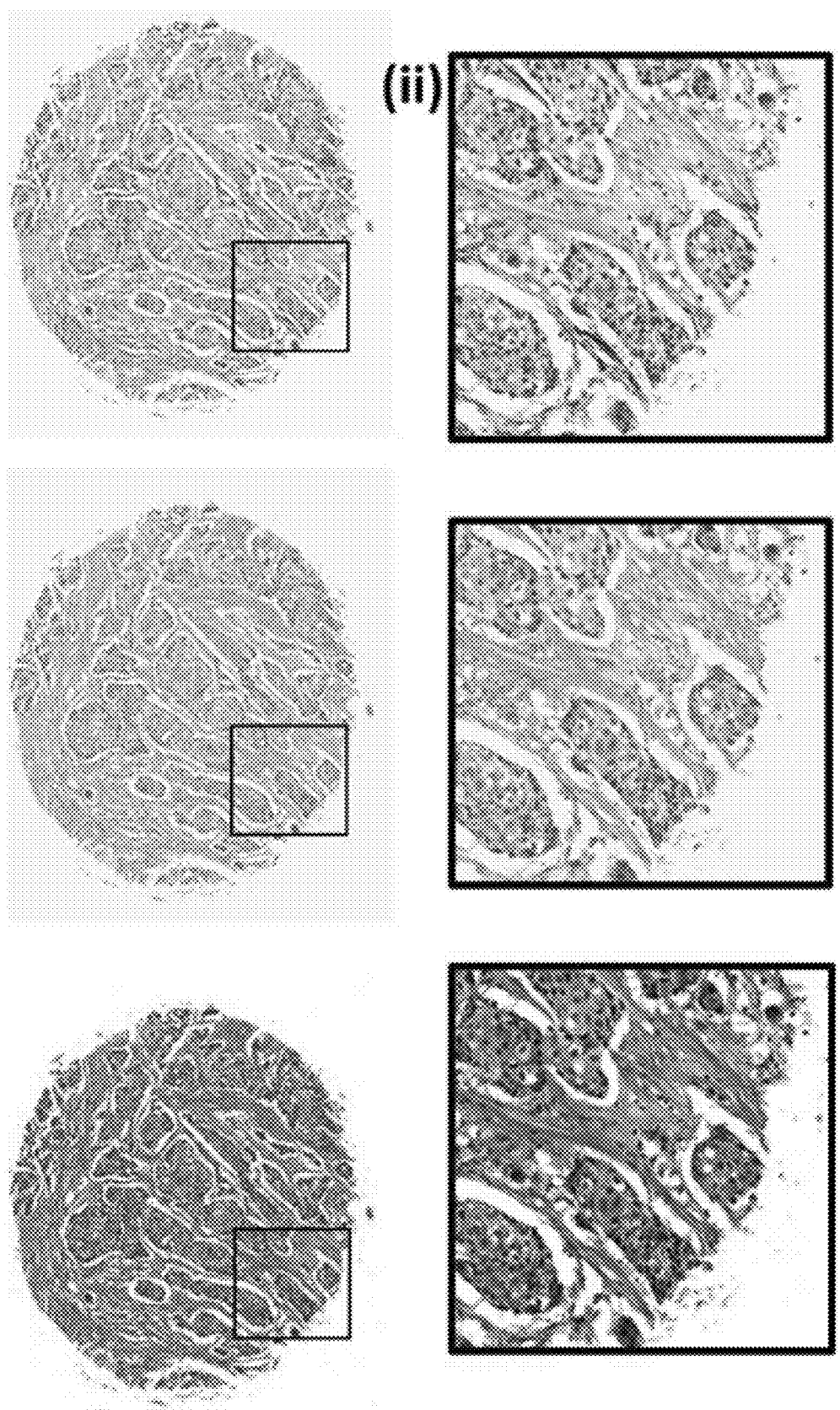
Figure 12C:
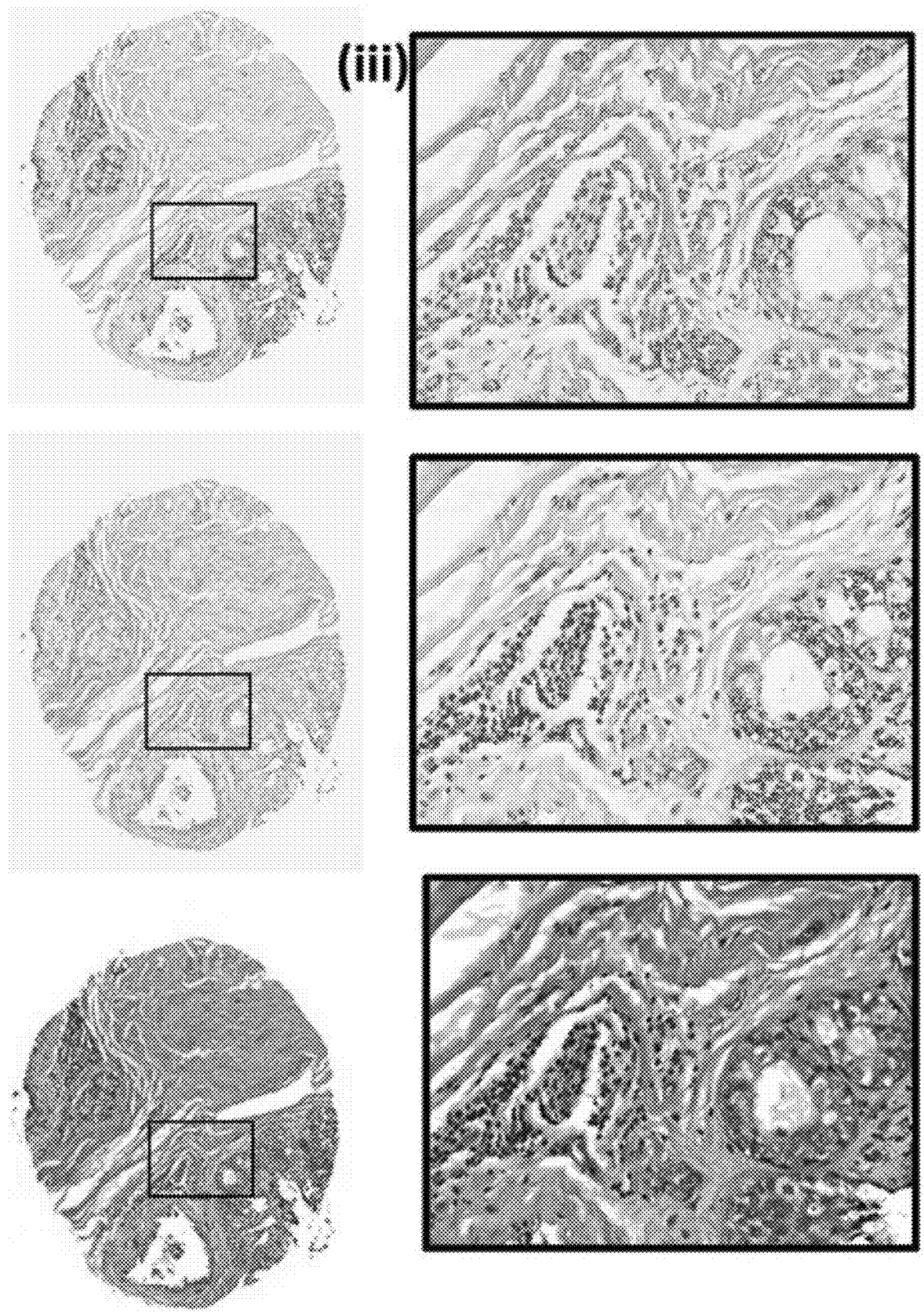

FIGS. 12A-12C show illustrate K-means clustering results overlaid on H&E stained images (gray scale) for test samples using five clusters. FIG. 12A shows a benign case with epithelial clustering (top), stromal clustering (middle), and H&E stained image (bottom). The inset (i) corresponds to zoomed in views from images in FIG. 12A. FIG. 12B shows a ductal carcinoma case with epithelial and stromal clustering along with the stained image, and where the inset (ii) corresponds to zoomed in views from images in FIG. 12B. FIG. 12C shows a lobular carcinoma case with clustering and ground truth comparison, and where the inset (iii) corresponds to zoomed regions from images in FIG. 12C.

It can be seen from the zoomed views in FIGS. 12A-12C that different signatures within the epithelial (top) and stromal (middle) regions are identified. It can also be noted (i.e., FIG. 12B in the zoomed region (ii) for the middle section) that cellular structures like lymphocytes, fibroblasts, and plasma cells that are typically present in the stroma get highlighted in the stromal clustering as a different class (e.g., a different color). This is advantageous because sometimes these components can be confused with epithelial cells and these cells constitute an important part of the tumor microenvironment. The systems and methods described in the present disclosure eliminate the confusion between epithelial and stromal cells by this two-tiered approach and provide a means to discover less abundant cells in the microenvironment.

Figure 13A:
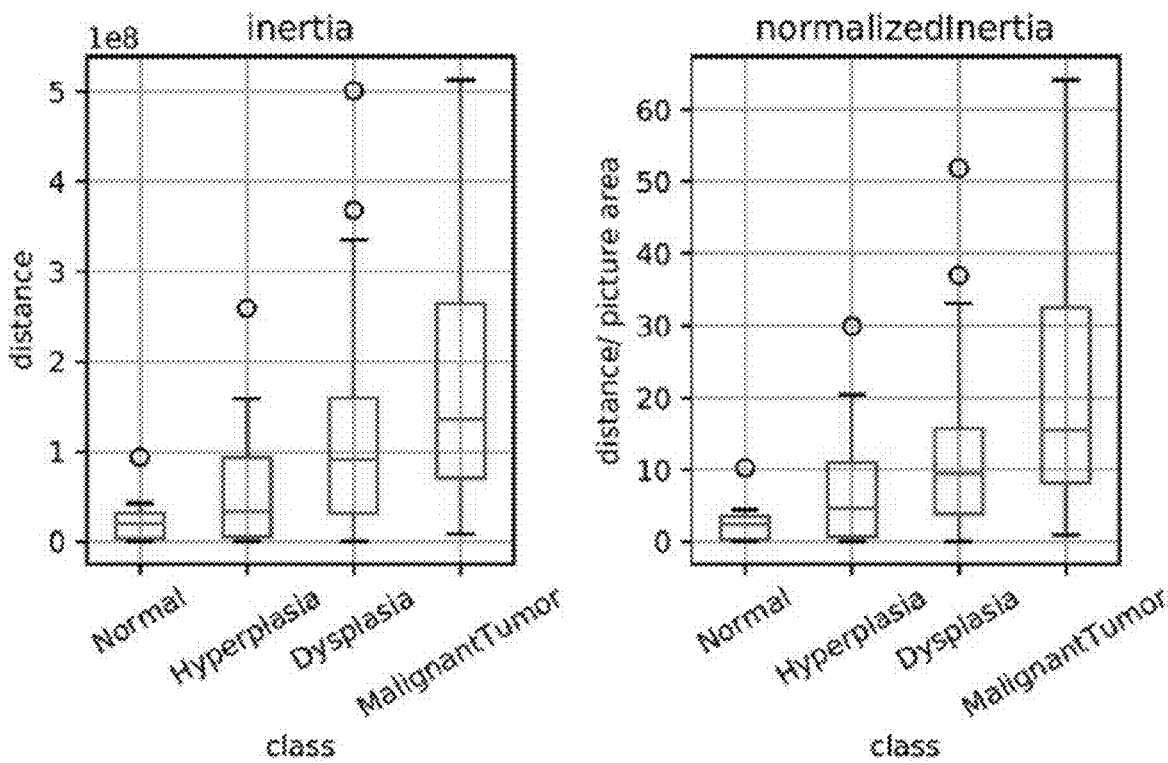
FIGS. 13A and 13B shows box plots for the calculated inertia (dispersion of points within a cluster) over tissue microarray images and for inertia divided by the image area (normalized), both for epithelium (FIG. 13A) and stroma (FIG. 13B). This illustrates the extent of differentiation in the epithelium and stromal compartments for different levels of disease states.
Figure 13B:
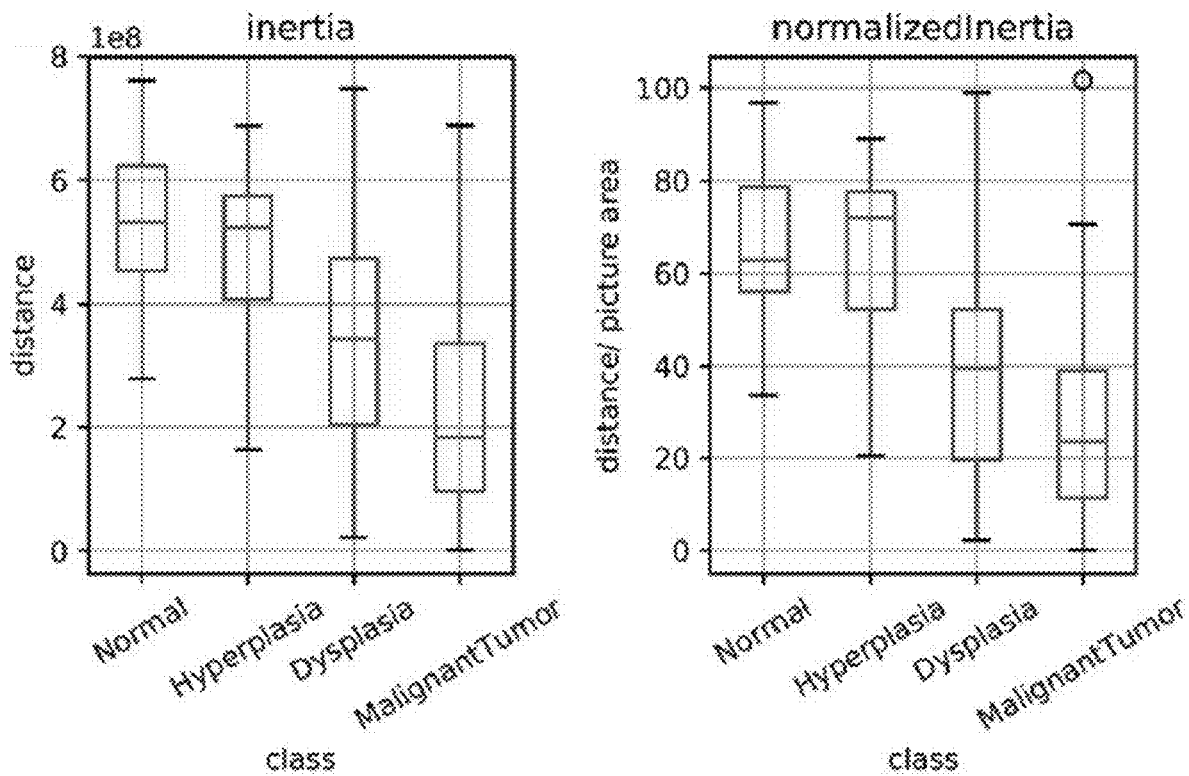

The unsupervised clusters are indicative of potential changes in the microenvironment. In this example study, it was further explored whether the clusters can help assist a clinician when diagnosing a disease. FIGS. 13A and 13B illustrate the spread of clusters (inertia) in the epithelial and stromal compartments for different disease states. Inertia is the within cluster sum of squares indicative of intra cluster coherence. For the epithelial distribution in FIG. 13A, the average inertia for the malignant class was the highest and the normal class was the lowest. Intraductal proliferations (e.g., hyperplasia and dysplasia) also follow the same trend with the high-risk group (e.g., dysplasia) having a higher mean inertia and the low-risk group (e.g., hyperplasia) having a lower inertia. This can help in increasing confidence of the diagnostic decision, especially because the histology criteria can be subjective and, in some cases, may not be clearly defined.

It is contemplated that disruption of normal physiologic structure of the tissue results in a difference in inertia, either by decreased order in consistent structures (e.g., changes in epithelial morphology) or imposition of homogeneity on well-differentiated functional units of tissue (e.g., tissue transitioning from clear functional units in a well-defined differentiated pattern to becoming poorly differentiated in space). As a result, the inertia parameters can be used as a basis for designing digital features that indicate disease. Though a single feature may not be unambiguous for any given sample, the trends can be useful in adding value to automated methods, provide a validation of designing digital markers using hypotheses of organization, and provide potential for further refinement.

Figure 14A:
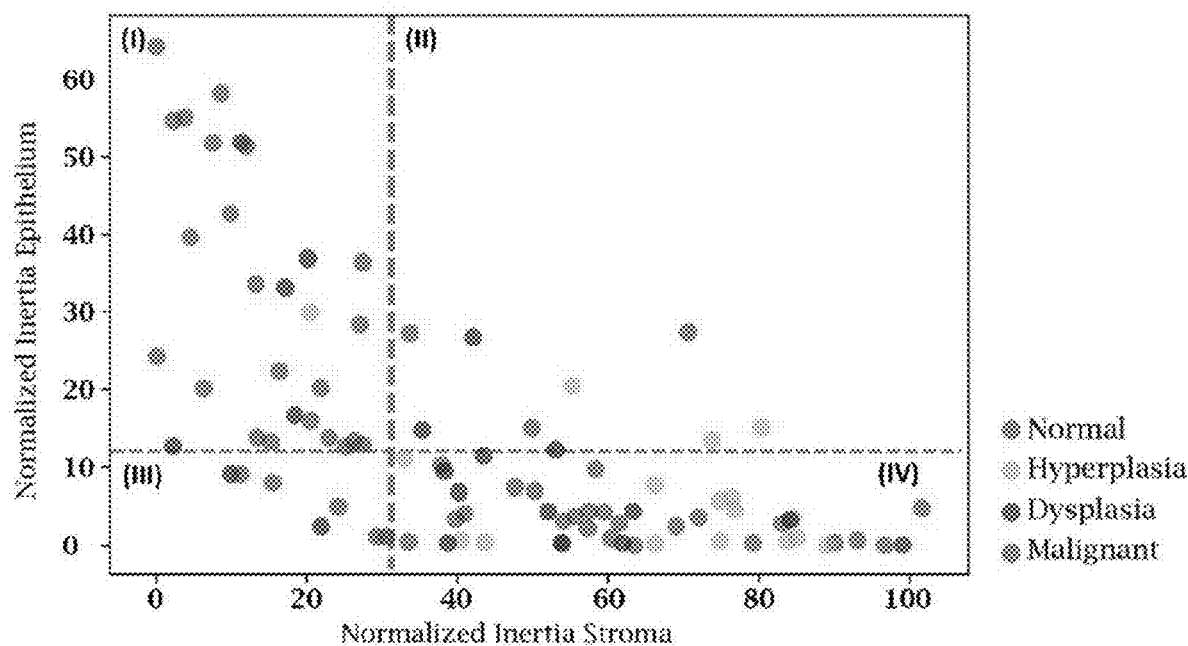
FIGS. 14A and 14B show cancer detection using both the epithelial and stromal spatial distributions in accordance with an embodiment of the present disclosure.

The use of both the epithelial and stromal inertia together was examined for diagnostic value. From the total of 100 cases in the example study, 8 patient cases either had insufficient epithelial or stromal yield. These were discarded as the epithelium and stromal inertia couldn't be compared. Therefore, an independent set of 92 patient cases belonging to different disease states was evaluated. The normalized inertia of the epithelial and stromal compartments were compared. By considering a cut-off line for each of the epithelial and stromal figures of merit, two intersecting lines were obtained, which divide the entire distribution of inertia into four quadrants. It can be seen from FIG. 14A that the normal and hyperplasia cases are mostly in quadrant IV and malignant cases are distributed in all the other quadrants with a majority lying in the first quadrant. The dotted lines can also be used as a threshold to separate cancer from the normal cases.

Figure 14B:
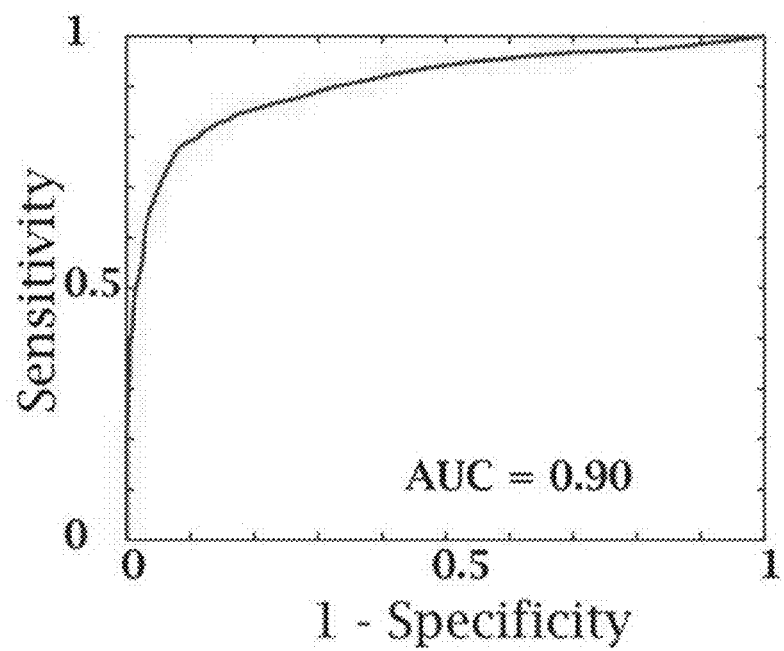

A variety of 2D thresholds can be used and the receiver operating characteristic curve in FIG. 14B shows the sensitivity and specificity profile of using inertia as a measure of detecting malignancy. For estimating the ROC curve, the malignant cases were labeled as the cancer class and all other categories (i.e., hyperplasia, dysplasia, and normal) were combined together into the non-cancer class. The area under the curve ("AU C") is a measure of the model performance and the closer it is to 1, the better the model. The high AUC values indicate that a combinatory epithelial and stromal approach to extract spatial features (inertia in this case) can be a good indicator of disease and its progression.

The results of this example study provide a useful means to utilize the microenvironment and ensure that the results are consistent with underlying diagnoses. Advantageously, the work paves the way for further assessment of complex cellular features in both epithelial cells as well as different stromal cells. Distribution of these cells and other spatial measures of the tumor can provide a further boost in accuracy to the methods disclosed in the present disclosure. An advantage of the disclosed method is that it is simple to understand and easy to interpret. Unlike a typical deep learning approach in which images are the input and a decision is the output, this tiered approach provides an insight to understand and interpret some of the vast information encoded in tissue on disease states.

Figure 15:
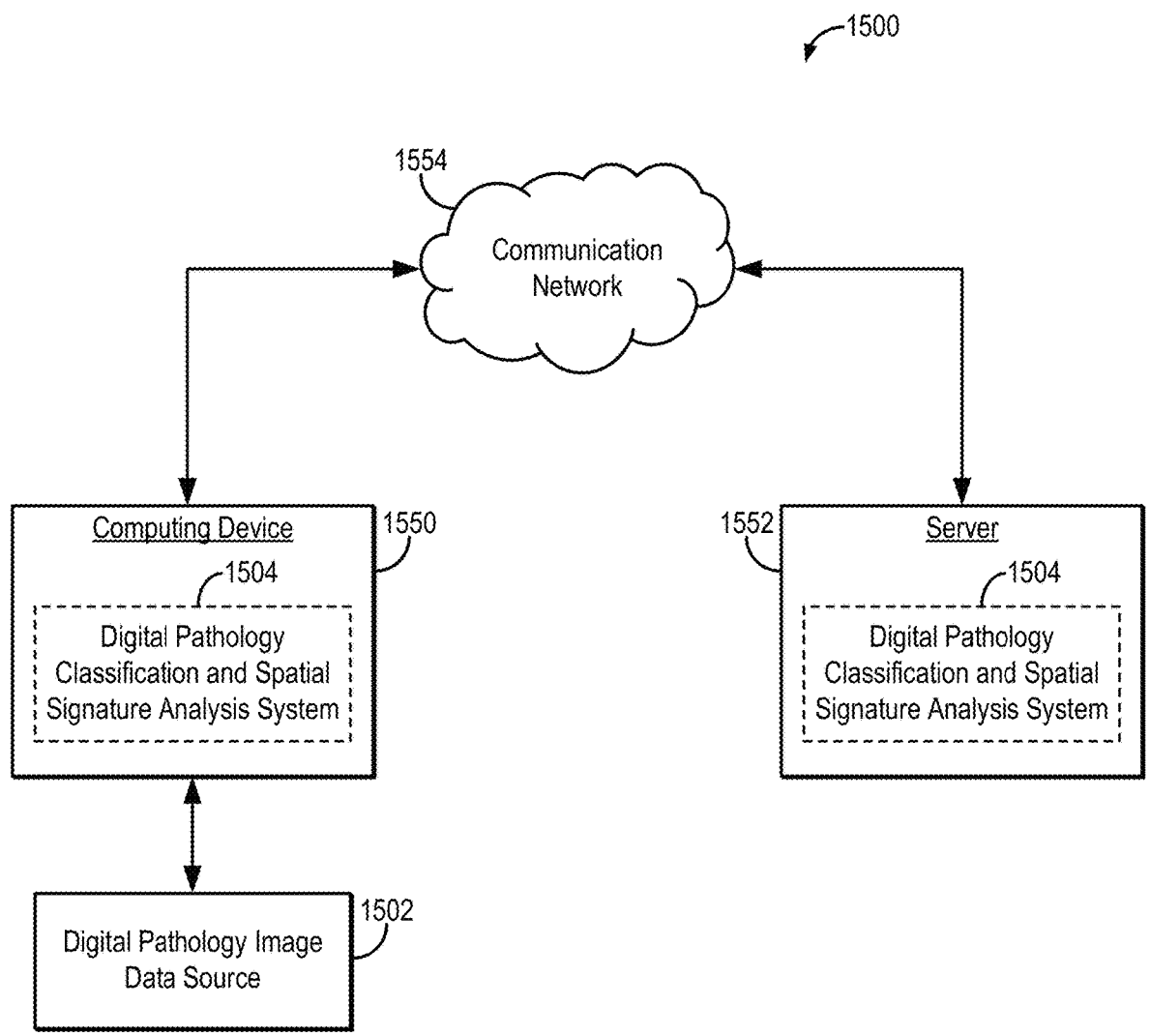
FIG. 15 is a block diagram of a system for classifying digital pathology image data using deep learning and providing a quantitative analysis of tumor and tissue microenvironment based on the classified feature data.

Referring now to FIG. 15, an example of a system 1500 for classifying digital pathology image data and providing a quantitative analysis of tumor and tissue microenvironment based on the classified feature data in accordance with some embodiments of the systems and methods described in the present disclosure is shown. As shown in FIG. 15, a computing device 1550 can receive one or more types of data (e.g., digital pathology image data, segmented digital pathology image data, annotated digital pathology image data, classified feature data, clustered feature data) from digital pathology image source 1502. In some embodiments, computing device 1550 can execute at least a portion of a digital pathology image classification and spatial feature analysis system 1504 to generate classified feature data, clustered feature data, and/or quantitative parameters (e.g., cluster inertia or other spatial features) from data received from the digital pathology image source 1502.

Additionally or alternatively, in some embodiments, the computing device 1550 can communicate information about data received from the digital pathology image source 1502 to a server 1552 over a communication network 1554, which can execute at least a portion of the digital pathology image classification and spatial feature analysis system 1504. In such embodiments, the server 1552 can return information to the computing device 1550 (and/or any other suitable computing device) indicative of an output of the digital pathology image classification and spatial feature analysis system 1504.

In some embodiments, computing device 1550 and/or server 1552 can be any suitable computing device or combination of devices, such as a desktop computer, a laptop computer, a smartphone, a tablet computer, a wearable computer, a server computer, a virtual machine being executed by a physical computing device, and so on. The computing device 1550 and/or server 1552 can also reconstruct images from the data.

In some embodiments, digital pathology image source 1502 can be any suitable source of image data (e.g., measurement data, images reconstructed from measurement data), such as a digital slide scanning system, another computing device (e.g., a server storing image data), and so on. In some embodiments, digital pathology image source 1502 can be local to computing device 1550. For example, digital pathology image source 1502 can be incorporated with computing device 1550 (e.g., computing device 1550 can be configured as part of a device for capturing, scanning, and/or storing images). As another example, digital pathology image source 1502 can be connected to computing device 1550 by a cable, a direct wireless link, and so on. Additionally or alternatively, in some embodiments, digital pathology image source 1502 can be located locally and/or remotely from computing device 1550, and can communicate data to computing device 1550 (and/or server 1552) via a communication network (e.g., communication network 1554).

In some embodiments, communication network 1554 can be any suitable communication network or combination of communication networks. For example, communication network 1554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 1554 can be a local area network, a wide area network, a public network (e.g., the Internet), a private or semi-private network (e.g., a corporate or university intranet), any other suitable type of network, or any suitable combination of networks. Communications links shown in FIG. 15 can each be any suitable communications link or combination of communications links, such as wired links, fiber optic links, Wi-Fi links, Bluetooth links, cellular links, and so on.

Figure 16:
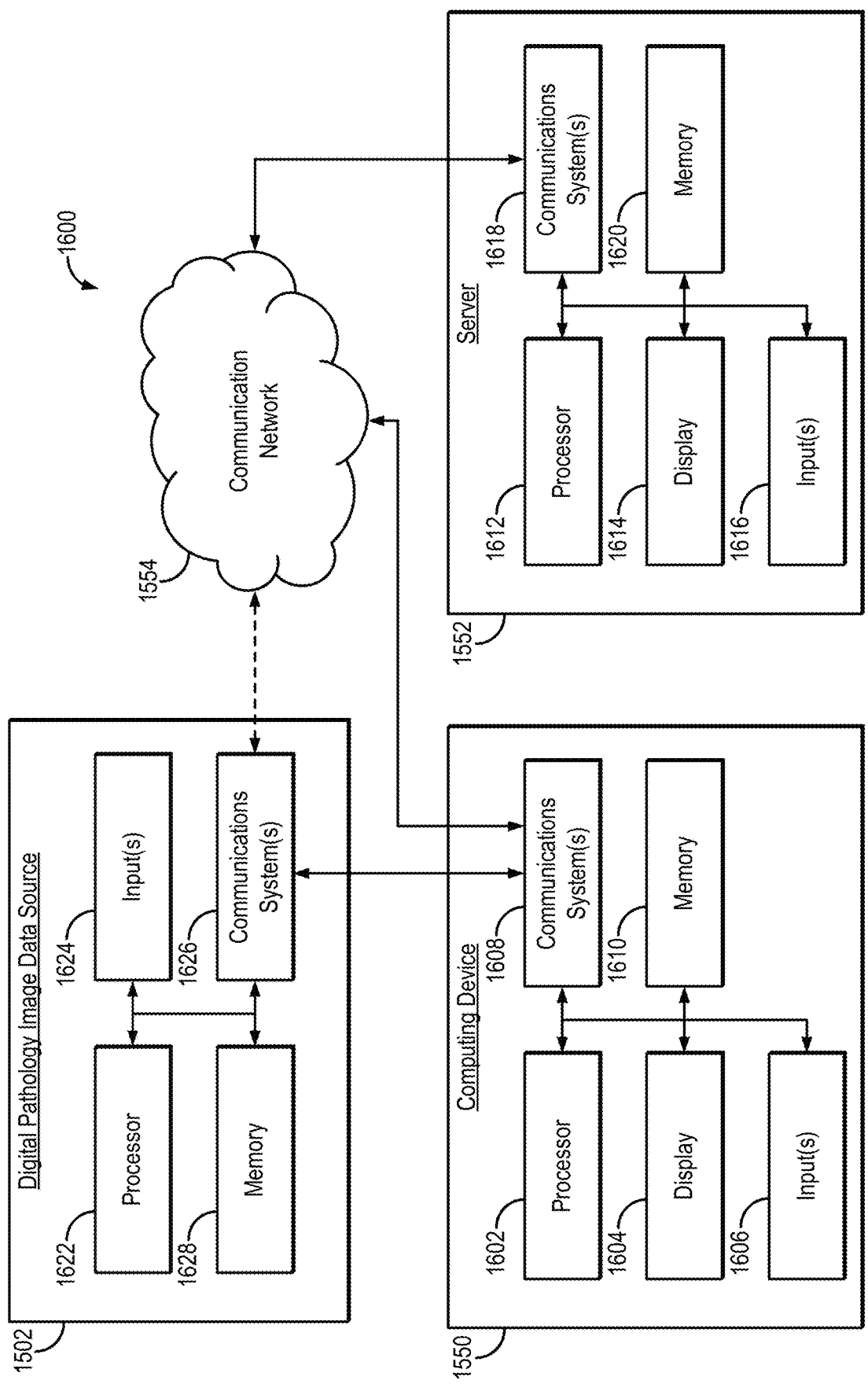
FIG. 16 is a block diagram of example components that can implement the system of FIG. 15.

Referring now to FIG. 16, an example of hardware 1600 that can be used to implement digital pathology image source 1502, computing device 1550, and server 1552 in accordance with some embodiments of the systems and methods described in the present disclosure is shown. As shown in FIG. 16, in some embodiments, computing device 1550 can include a processor 1602, a display 1604, one or more inputs 1606, one or more communication systems 1608, and/or memory 1610. In some embodiments, processor 1602 can be any suitable hardware processor or combination of processors, such as a central processing unit ("CPU"), a graphics processing unit ("GPU"), and so on. In some embodiments, display 1604 can include any suitable display devices, such as a computer monitor, a touchscreen, a television, and so on. In some embodiments, inputs 1606 can include any suitable input devices and/or sensors that can be used to receive user input, such as a keyboard, a mouse, a touchscreen, a microphone, and so on.

In some embodiments, communications systems 1608 can include any suitable hardware, firmware, and/or software for communicating information over communication network 1554 and/or any other suitable communication networks. For example, communications systems 1608 can include one or more transceivers, one or more communication chips and/or chip sets, and so on. In a more particular example, communications systems 1608 can include hardware, firmware and/or software that can be used to establish a Wi-Fi connection, a Bluetooth connection, a cellular connection, an Ethernet connection, and so on.

In some embodiments, memory 1610 can include any suitable storage device or devices that can be used to store instructions, values, data, or the like, that can be used, for example, by processor 1602 to present content using display 1604, to communicate with server 1552 via communications system(s) 1608, and so on. Memory 1610 can include any suitable volatile memory, non-volatile memory, storage, or any suitable combination thereof. For example, memory 1610 can include RAM, ROM, EEPROM, one or more flash drives, one or more hard disks, one or more solid state drives, one or more optical drives, and so on. In some embodiments, memory 1610 can have encoded thereon, or otherwise stored therein, a computer program for controlling operation of computing device 1550. In such embodiments, processor 1602 can execute at least a portion of the computer program to present content (e.g., images, user interfaces, graphics, tables), receive content from server 1552, transmit information to server 1552, and so on.

In some embodiments, server 1552 can include a processor 1612, a display 1614, one or more inputs 1616, one or more communications systems 1618, and/or memory 1620. In some embodiments, processor 1612 can be any suitable hardware processor or combination of processors, such as a CPU, a GPU, and so on. In some embodiments, display 1614 can include any suitable display devices, such as a computer monitor, a touchscreen, a television, and so on. In some embodiments, inputs 1616 can include any suitable input devices and/or sensors that can be used to receive user input, such as a keyboard, a mouse, a touchscreen, a microphone, and so on.

In some embodiments, communications systems 1618 can include any suitable hardware, firmware, and/or software for communicating information over communication network 1554 and/or any other suitable communication networks. For example, communications systems 1618 can include one or more transceivers, one or more communication chips and/or chip sets, and so on. In a more particular example, communications systems 1618 can include hardware, firmware and/or software that can be used to establish a Wi-Fi connection, a Bluetooth connection, a cellular connection, an Ethernet connection, and so on.

In some embodiments, memory 1620 can include any suitable storage device or devices that can be used to store instructions, values, data, or the like, that can be used, for example, by processor 1612 to present content using display 1614, to communicate with one or more computing devices 1550, and so on. Memory 1620 can include any suitable volatile memory, non-volatile memory, storage, or any suitable combination thereof. For example, memory 1620 can include RAM, ROM, EEPROM, one or more flash drives, one or more hard disks, one or more solid state drives, one or more optical drives, and so on. In some embodiments, memory 1620 can have encoded thereon a server program for controlling operation of server 1552. In such embodiments, processor 1612 can execute at least a portion of the server program to transmit information and/or content (e.g., data, images, a user interface) to one or more computing devices 1550, receive information and/or content from one or more computing devices 1550, receive instructions from one or more devices (e.g., a personal computer, a laptop computer, a tablet computer, a smartphone), and so on.

In some embodiments, digital pathology image source 1502 can include a processor 1622, one or more image acquisition systems 1624, one or more communications systems 1626, and/or memory 1628. In some embodiments, processor 1622 can be any suitable hardware processor or combination of processors, such as a CPU, a GPU, and so on. In some embodiments, the one or more image acquisition systems 1624 are generally configured to acquire data, images, or both, and can include a digital slide scanning system. Additionally or alternatively, in some embodiments, one or more image acquisition systems 1624 can include any suitable hardware, firmware, and/or software for coupling to and/or controlling operations of a digital slide scanning system. In some embodiments, one or more portions of the one or more image acquisition systems 1624 can be removable and/or replaceable.

Note that, although not shown, digital pathology image source 1502 can include any suitable inputs and/or outputs. For example, digital pathology image source 1502 can include input devices and/or sensors that can be used to receive user input, such as a keyboard, a mouse, a touchscreen, a microphone, a trackpad, a trackball, and so on. As another example, digital pathology image source 1502 can include any suitable display devices, such as a computer monitor, a touchscreen, a television, etc., one or more speakers, and so on.

In some embodiments, communications systems 1626 can include any suitable hardware, firmware, and/or software for communicating information to computing device 1550 (and, in some embodiments, over communication network 1554 and/or any other suitable communication networks). For example, communications systems 1626 can include one or more transceivers, one or more communication chips and/or chip sets, and so on. In a more particular example, communications systems 1626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1628 can include any suitable storage device or devices that can be used to store instructions, values, data, or the like, that can be used, for example, by processor 1622 to control the one or more image acquisition systems 1624, and/or receive data from the one or more image acquisition systems 1624; to images from data; present content (e.g., images, a user interface) using a display; communicate with one or more computing devices 1550; and so on. Memory 1628 can include any suitable volatile memory, non-volatile memory, storage, or any suitable combination thereof. For example, memory 1628 can include RAM, ROM, EEPROM, one or more flash drives, one or more hard disks, one or more solid state drives, one or more optical drives, and so on. In some embodiments, memory 1628 can have encoded thereon, or otherwise stored therein, a program for controlling operation of digital pathology image source 1502. In such embodiments, processor 1622 can execute at least a portion of the program to generate images, transmit information and/or content (e.g., data, images) to one or more computing devices 1550, receive information and/or content from one or more computing devices 1550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Certain operations of methods according to the disclosure, or of systems executing those methods, may be represented schematically in the figures or otherwise discussed herein. Unless otherwise specified or limited, representation in the figures of particular operations in particular spatial order may not necessarily require those operations to be executed in a particular sequence corresponding to the particular spatial order. Correspondingly, certain operations represented in the figures, or otherwise disclosed herein, can be executed in different orders than are expressly illustrated or described, as appropriate for particular embodiments of the disclosure. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, unless otherwise defined or limited, the phase "and/or" used with two or more items is intended to cover the items individually and both items together. For example, a device having "a and/or b" is intended to cover: a device having a (but not b); a device having b (but not a); and a device having both a and b.

The present disclosure has described one or more preferred embodiments, and it should be appreciated that many equivalents, alternatives, variations, and modifications, aside from those expressly stated, are possible and within the scope of the invention.

The invention claimed is:

1. A method for characterizing a tissue based on analysis of digital pathology images of the tissue, the method comprising:
   (a) accessing segmented digital pathology image data with a computer system, wherein the segmented digital pathology image data comprise digital pathology images of a tissue that have been segmented into two or more different cellular compartments of the tissue;
   (b) applying the segmented digital pathology image data to a clustering algorithm using the computer system, generating output as clustered feature data comprising clusters of the segmented digital pathology image data that indicate separated tissue microenvironment components of the tissue;
   (c) computing spatial feature parameter data for clusters in the clustered feature data using the computer system; and
   (d) generating a report with the computer system, wherein the report characterizes the tissue based on the spatial feature parameter data, wherein the report indicates a likelihood of disease in the tissue.

2. The method of claim 1, wherein the two or more different cellular components include epithelial and stromal compartments.

3. The method of claim 1, wherein the tissue microenvironment components include at least one of immune cells and cancer associated with fibroblasts.

4. The method of claim 1, wherein the clustering algorithm is an unsupervised clustering algorithm.

5. The method of claim 4, wherein the unsupervised clustering algorithm is a K-mean clustering algorithm.

6. The method of claim 5, wherein the K-mean clustering algorithm uses a number of clusters ranging from two to five clusters.

7. The method of claim 1, wherein the tissue is breast tissue.

8. The method of claim 1, wherein accessing the segmented digital pathology image data with the computer system comprises:
   accessing digital pathology image data with the computer system, wherein the digital pathology image data comprise digital pathology images of the tissue; and
   segmenting the digital pathology image data with the computer system, generating output as the segmented digital pathology image data.

9. The method of claim 8, wherein segmenting the digital pathology image data with the computer system comprises:
   accessing a deep learning model with the computer system, wherein the deep learning model has been trained to segment digital pathology images into different cellular components; and
   applying the digital pathology image data to the deep learning model using the computer system, generating output as the segmented digital pathology image data.

10. The method of claim 9, wherein the deep learning model is a convolutional neural network (CNN) model.

11. The method of claim 10, wherein the CNN model has been trained on hematoxylin and eosin (H&E) stained images.

12. The method of claim 11, wherein the H&E stained images used to train the CNN model comprise H&E images obtained from specimens including normal breast tissue, usual hyperplasia, atypical hyperplasia with columnar change, and atypical hyperplasia without columnar change, and ductal carcinoma in-situ.

13. The method of claim 1, wherein computing the spatial feature parameter data for clusters in the clustered feature data comprise computing inertia for clusters in the clustered feature data.

14. The method of claim 13, wherein the report characterizes the tissue based on the inertia computed for the clusters in the clustered feature data.

15. The method of claim 14, wherein the two or more different cellular components include epithelial and stromal compartments, and the report characterizes the tissue based on the inertia computed for clusters in at least one of the epithelial compartment and the stromal compartment.

16. The method of claim 15, wherein the report characterizes the tissue based on the inertia computed for both the epithelial compartment and the stromal compartment.

17. The method of claim 1, wherein the report identifies spatial characteristics of early stage disease that are indicative of triaging biopsies from the tissue.

* * * * *